(12) United States Patent
Gardella et al.

(10) Patent No.: US 12,343,197 B2
(45) Date of Patent: Jul. 1, 2025

(54) SYSTEMS AND METHODS FOR IMPROVING DETECTION OF FETAL CONGENITAL HEART DEFECTS

(71) Applicant: BrightHeart SAS, Paris (FR)

(72) Inventors: Christophe Gardella, Paris (FR); Valentin Thorey, Paris (FR); Eric Askinazi, Paris (FR); Olivier Tranzer, Paris (FR); Marilyne Levy, Paris (FR); Bertrand Stos, Le Plessis Robinson (FR); Cécile Dupont, Paris (FR)

(73) Assignee: BrightHeart SAS, Paris (FR)

( * ) Notice: Subject to any disclaimer, the term of this patent is extended or adjusted under 35 U.S.C. 154(b) by 0 days.

(21) Appl. No.: 18/828,923

(22) Filed: Sep. 9, 2024

(65) Prior Publication Data

US 2024/0423583 A1    Dec. 26, 2024

Related U.S. Application Data

(63) Continuation-in-part of application No. 18/406,446, filed on Jan. 8, 2024, now Pat. No. 12,082,969, which (Continued)

(30) Foreign Application Priority Data

Feb. 22, 2023   (EP) ..................... 23305235

(51) Int. Cl.
*G06T 7/00* (2017.01)
*A61B 8/00* (2006.01)
(Continued)

(52) U.S. Cl.
CPC .......... *A61B 8/0866* (2013.01); *A61B 8/5223* (2013.01); *G06T 7/0012* (2013.01);
(Continued)

(58) Field of Classification Search
CPC ............... A61B 8/0866; A61B 8/5223; A61B 2576/023; G06T 7/0012;
(Continued)

(56) References Cited

U.S. PATENT DOCUMENTS 7,672,491 B2   3/2010   Krishnan et al.
11,478,222 B2  10/2022  Shiran et al.
(Continued)

FOREIGN PATENT DOCUMENTS

CN   114469176 A   5/2022
CN   114677754 A   6/2022
(Continued)

OTHER PUBLICATIONS

U.S. Appl. No. 18/183,937 / U.S. Pat. No. 11,869,188, filed Mar. 14, 2023 / Jan. 9, 2024.
(Continued)

*Primary Examiner* — Van D Huynh
(74) *Attorney, Agent, or Firm* — Greenberg Traurig, LLP; Christopher C. Bolten; Robert D. Ward

(57) ABSTRACT

Systems and methods are provided for aiding the detection and diagnosis of critical heart defects during fetal ultrasound examinations, in which image data (e.g., motion video clips and/or image frames) is analyzed with machine learning algorithms to detect and identify morphological and/or flow abnormalities indicative of critical CHDs. The results of the analyses are presented for review to the clinician, optionally with an overlay, for the selected image frames that identifies the abnormalities with graphical or textual indicia. The overlay further may be annotated by the clinician and stored to create documentary record of the fetal ultrasound examination.

20 Claims, 14 Drawing Sheets

Related U.S. Application Data is a continuation-in-part of application No. 18/183,937, filed on Mar. 14, 2023, now Pat. No. 11,869,188.

(60) Provisional application No. 63/584,117, filed on Sep. 20, 2023.

(51) Int. Cl.
| | |
|---|---|
| *A61B 8/08* | (2006.01) |
| *G16H 50/20* | (2018.01) |
| *G16H 50/30* | (2018.01) |
| *G16H 30/20* | (2018.01) |

(52) U.S. Cl.
CPC ............ *G16H 50/20* (2018.01); *G16H 50/30* (2018.01); *A61B 2576/023* (2013.01); *G06T 2207/10016* (2013.01); *G06T 2207/10132* (2013.01); *G06T 2207/20084* (2013.01); *G06T 2207/30044* (2013.01); *G06T 2207/30048* (2013.01); *G16H 30/20* (2018.01)

(58) Field of Classification Search
CPC . G06T 2207/10016; G06T 2207/10132; G06T 2207/20084; G06T 2207/30044; G06T 2207/30048; G16H 50/20; G16H 50/30; G16H 30/20
See application file for complete search history.

(56) References Cited

U.S. PATENT DOCUMENTS

| | | | |
|---|---|---|---|
| 11,488,298 | B2 | 11/2022 | Annangi et al. |
| 11,517,290 | B2 | 12/2022 | Aase et al. |
| 11,861,838 | B1 | 1/2024 | Gardella |
| 11,869,188 | B1 | 1/2024 | Levy et al. |
| 11,875,507 | B1 | 1/2024 | Gardella et al. |
| 2005/0004465 | A1 | 1/2005 | Abuhamad |
| 2005/0245825 | A1* | 11/2005 | Krantz ................. G06T 7/66 600/443 |
| 2005/0251013 | A1 | 11/2005 | Krishnan et al. |
| 2005/0251036 | A1* | 11/2005 | Abuhamad .......... A61B 8/0866 600/443 |
| 2005/0267376 | A1* | 12/2005 | Marossero ............ A61B 5/349 600/511 |
| 2014/0050384 | A1 | 2/2014 | Schmidt et al. |
| 2017/0337731 | A1* | 11/2017 | Jago .................... A61B 8/483 |
| 2018/0206819 | A1* | 7/2018 | Saarinen ............. A61B 8/0866 |
| 2020/0155114 | A1* | 5/2020 | Park .................... A61B 8/463 |
| 2020/0202502 | A1 | 6/2020 | Tsymbalenko |
| 2020/0202551 | A1* | 6/2020 | Ciofolo-Veit ........ A61B 8/5223 |
| 2020/0214618 | A1* | 7/2020 | Vullings ............... G16H 50/20 |
| 2020/0219274 | A1 | 7/2020 | Afridi et al. |
| 2020/0345261 | A1* | 11/2020 | Haeusser .............. A61B 5/361 |
| 2021/0034587 | A1 | 2/2021 | Arye et al. |
| 2021/0150693 | A1* | 5/2021 | Fornwalt .............. G06N 3/045 |
| 2021/0202069 | A1* | 7/2021 | van der Veen ........ G16H 50/20 |
| 2021/0280298 | A1 | 9/2021 | Samset et al. |
| 2021/0319558 | A1 | 10/2021 | Min et al. |
| 2021/0345987 | A1 | 11/2021 | Ciofolo-Veit et al. |
| 2022/0012875 | A1* | 1/2022 | Arnaout ............... G06F 18/217 |
| 2022/0142609 | A1* | 5/2022 | Yeo ..................... A61B 8/461 |
| 2022/0361799 | A1* | 11/2022 | Hong ................... A61B 5/7267 |
| 2023/0064623 | A1* | 3/2023 | Krishnan ............. A61B 8/0883 |
| 2023/0135046 | A1* | 5/2023 | Liu ...................... G06T 7/0016 600/440 |
| 2023/0394655 | A1* | 12/2023 | Ben Bashat ......... A61B 5/4064 |
| 2024/0423583 | A1* | 12/2024 | Gardella ............... G16H 50/30 |

FOREIGN PATENT DOCUMENTS

| | | |
|---|---|---|
| CN | 115424335 A | 12/2022 |
| EP | 3964136 A1 | 3/2022 |
| EP | 4144301 A1 | 3/2023 |
| WO | WO-2022265345 A1 | 12/2022 |

OTHER PUBLICATIONS

U.S. Appl. No. 18/183,942 / U.S. Pat. No. 11,875,507, filed Mar. 14, 2023 / Jan. 16, 2024.
U.S. Appl. No. 18/330,819 / U.S. Pat. No. 11,861,838, filed Jun. 7, 2023 / Jan. 2, 2024.
U.S. Appl. No. 18/406,446 / U.S. Pat. No. 12,082,969, filed Jan. 8, 2024 Sep. 10, 2024.
U.S. Appl. No. 18/412,325, filed Jan. 12, 2024.
International Search Report & Written Opinion dated Sep. 18, 2024 in Int'l PCT Patent Appl. Serial No. PCT/IB2024/054937 (031001).
Abuhamad A., et al., "Obstetric and Gynecologic Ultrasound Curriculum and Competency Assessment in Residency Training Programs: Consensus Report: Obstetric and Gynecologic Ultrasound Training," Journal of Ultrasound in Medicine, vol. 37(1):19-50, DOI:10.1002/jum.14519 (Jan. 2018).
Activity recognition, Wikipedia The Free Encyclopedia, retrieved from the internet URL: https://en.wikipedia.org/wiki/Activity_recognition, 12 pages (2018).
"AIUM Practice Guideline for the Performance of Fetal Echocardiography," Fetal Echocardiography Task Force; American Institute of Ultrasound in Medicine Clinical Standards Committee; American College of Obstetricians and Gynecologists; Society for Maternal-fetal Medicine, Journal of Ultrasound in Medicine, vol. 30(1):27-136, doi:10.7863/jum.2011.30.1.127 (Jan. 2011).
AIUM-ACR-ACOG-SMFM-SRU Practice Parameter for the Performance of Standard Diagnostic Obstetric Ultrasound Examination, J. Ultrasound Med., 37:E13-E24 (2018).
Alom, et al., The History Began from AlexNet: A Comprehensive Survey on Deep Learning Approaches, retrieved from the internet URL: https://arxiv.org/abs/1803.01164, 39 pages (2018).
Arnaout, et al., An Ensemble of Neural Networks Provides Expert-Level Prenatal Detection of Complex Congenital Heart Disease, *Nature Medicine*, 27(5):882-891 (May 2021).
Arnaout, et al., An ensemble of neural networks provides expert-level prenatal detection of complex congenital heart disease, Nature Medicine, 27(5):882-91 (May 2021).
Arth et al., "Inpatient Hospitalization Costs Associated with Birth Defects Among Persons of All Ages-United States, 2013," MMWR Morbidity and Mortality Weekly Report, vol. 66(2):41-46, DOI:10.15585/mmwr.mm6602a1. (Jan. 20, 2017).
Berghella V., et al., "Accuracy of Prenatal Diagnosis of Congenital Heart Defects," Fetal Diagnosis and Therapy, vol. 16(6):407-412, DOI:10.1159/000053949. (Mar. 2001).
Bjornard K., et al., "Patterns in the Prevalence of Congenital Heart Defects, Metropolitan Atlanta, 1978 to 2005," Birth Defects Research. (Part A): Clinical and Molecular Teratology, vol. 97(2):87-94, doi:10.1002/bdra.23111 (Feb. 2013).
Bonnet D., et al., "Detection of Transposition of the Great Arteries in Fetuses Reduces Neonatal Morbidity and Mortality," Circulation, vol. 99(7):916-918, DOI:10.1161/01.cir.99.7.916. (Feb. 1999).
Cardinal M., et al., "Incremental Detection of Severe Congenital Heart Disease by Fetal Echocardiography Following a Normal Second Trimester Ultrasound Scan in Québec, Canada," Circulation. Cardiovascular Imaging, vol. 15(4):240-248, doi:10.1161/CIRCIMAGING.121.013796 (Apr. 2022).
Carreira, et al., Quo Vadis, Action Recognition? A New Model and the Kinetics Dataset, retrieved from the internet URL: https://arxiv.org/abs/1705.07750, 10 pages (2018).
Carvalho, et al., ISUOG Practice Guidelines (updated): sonorgraphic screening examination of the fetal heart, Ultrasound Obstet. Gynecol., 41:348-359 (2013).
Carvalho J.S., et al., "ISUOG Practice Guidelines (updated): fetal cardiac screening," Ultrasound Obstet Gynecol, vol. 61(6):788-803, DOI:10.1002/uog.26224. (Jun. 2023).
Centers for Disease Control and Prevention (CDC), "Racial Differences by Gestational Age in Neonatal Deaths Attributable to Congenital Heart Defects—United States, 2003-2006," Morbidity and Mortality Weekly Report (MMWR), vol. 59(37):1208-1211 (Sep. 2010).

(56) References Cited

OTHER PUBLICATIONS

Cluster, Construct Clusters from Gaussian Mixture Distribution, retrieved from the internet URL: https://www.mathworks.com/help/stats/gmdistribution.cluster.html, 6 pages, retrieved on Apr. 13, 2023.

Cluster Gaussian Mixture Data Using Hard Clustering, retrieved from the internet URL: https://www.mathworks.com/help/stats/cluster-data-from-mixture-of-gaussian-distributions.html, retrieved on Apr. 13, 2023, 6 pages.

Cluster Gaussian Mixture Data Using Soft Clustering, retrieved from the internet URL: https://www.mathworks.com/help/stats/cluster-gaussian-mixture-data-using-soft-clustering.html, retrieved on Apr. 13, 2023, 5 pages.

Create Gaussian Mixture Model, retrieved from the internet URL: https://www.mathworks.com/help/stats/gmdistribution.html#mw_132ef7d2-0aa5-498f-bd6e-824f3edc8567, retrieved on Apr. 13, 2023, 8 pages.

Data Sets, UCF101—Action Recognition Data Set, UCF Center for Research in Computer Vision, 6 pages (2012).

Day, et al., Artificial Intelligence, Fetal Echocardiograhy, and Congenital Heart Disease, Prenatal Diagnosis, 41(6):733-42 (May 2021).

Donofrio, et al., Diagnosis and Treatment of Fetal Cardiac Disease, A Scientific Statement From the American Heart Association, *Circulation*, 129(21):2183-242 (May 2014).

Eckersley L., et al., "Timing of Diagnosis Affects Mortality in Critical Congenital Heart Disease," Archives of Disease in Childhood, vol. 101(6):516-520, doi:10.1136/archdischild-2014-307691 (Jun. 2016).

Espinoza J., et al., "The Role of the Sagittal View of the Ductal Arch in Identification of Fetuses With Conotruncal Anomalies Using 4-Dimensional Ultrasonography," J Ultrasound Med., vol. 26(9):1181-1188, doi:10.7863/jum.2007.26.9.1181 (Sep. 2007).

Feichtenhofer, et al., Convolutional Two-Stream Network Fusion for Video Action Recognition, retrieved from the internet URL: https://arxiv.org/abs/1604.06573, 9 pages (2016).

Feichtenhofer, et al., Slow Fast Networks for Video Recognition, retrieved from the internet URL: hhttps://arxiv.org/abs/1812.03982, 10 pages (2019).

Feichtenhofer, et al., Spatiotemporal Residual Networks for Video Action Recognition, retrieved from the internet URL: https://arxiv.org/abs/1611.02155, 9 pages (2016).

Feng, et al., Two-Stream Attention Spatio-Temporal Network For Classification of Echocardiography Videos, 2021 IEEE 18th International Symposium on Biomedical Imaging (ISBI), pp. 1461-1465 (Apr. 2021).

Fiorentino, et al., A Review on Deep-Learning Algorithms for Fetal Ultrasound-Image Analysis, Medical Image Analysis, 1:83 102629 (Jan. 2023).

Fitgmdist, Fit Gaussian Mixture Model to Data, MATLAB fitgmdist, retrieved from the internet URL: https://www.mathworks.com/help/stats/fitgmdist.html, retrieved on Apr. 13, 2023, 17 pages.

Friedberg M.K., et al., "Prenatal Detection of Congenital Heart Disease," The Journal of Pediatrics, vol. 155(1):26-31, doi:10.1016/j.jpeds.2009.01.050 (Jul. 2009).

Gao, et al., A fused deep learning architecture for viewpoint classification of echocardiography, 36:103-13 (Jul. 2017).

Gao, et al., Detection and Characterization of the Fetal Heartbeat in Free-hand Ultrasound Sweeps with Weakly-Supervised Two-Streams Convolutional Networks, *Medical Image Computing and Computer-Assisted Intervention—MICCAI 2017, 20th International Conference Proceedings, Part II* 20, pp. 305-313, (Sep. 2017).

Gao, et al., Fast Video Multi-Style Transfer, IEEE Winter Conference on Applications of Computer Vision (WACV), pp. 3222-3230 (2020).

Gatys, et al., A Neural Algorithm of Artistic Style, retrieved from the internet URL: https://arxiv.org/abs/1508.06576, 16 pages (2015).

Gkioxari, et al., Finding Action Tubes, retrieved from internet URL: https://arxiv.org/abs/1411.6031, 10 pages (Nov. 2014).

Goodale, et al., Separate Visual Pathways for Perception and Action, Trends in Neurosciences, 15(1):20-25 (Jan. 1992).

Grandjean, et al., The performance of routine ultrasonographic screening of pregnancies in the Eurofetus Study, American Journal of Obstetrics and Gynecology, 181(2):446-454 (Aug. 1999).

He, et al., Deep Residual Learning for Image Recognition, In Proceedings of the IEEE Conference on Computer Vision and Pattern Recognition, pp. 770-778 (2016).

He R., et al., "Examining Contributing Factors to Accuracy of Fetal Echocardiography in Prenatal Diagnosis of Congenital Heart Disease," Journal of the American College of Cardiology, vol. 77(18):502, DOI:10.1016/S0735-1097(21)01861-1. (May 2021).

HMDB: A Large Human Motion Database, Serre Lab, retrieved from the internet URL: https://serre-lab.clps.brown.edu/resource/hmdb-a-large-human-motion-database/, accessed on Mar. 23, 2023, 6 pages.

Hoffman J.I.E., et al., "The Incidence of Congenital Heart Disease," Journal of the American College of Cardiology, vol. 39(12):1890-1900, doi:10.1016/S0735-1097(02)01886-7 (Jun. 19, 2002).

Holland B.J., et al., "Prenatal diagnosis of critical congenital heart disease reduces risk of death from cardiovascular compromise prior to planned neonatal cardiac surgery: a meta-analysis," Ultrasound Obstet Gynecol, vol. 45(6):631-638, DOI:10.1002/uog.14882. (Jun. 2015).

Howard, et al., Improving Ultrasound Video Classification: an Evaluation of Novel Deep Learning Methods in Echocardiography, Journal of Medical Artificial Intelligence, 14 pages (Mar. 2020).

Huang, Real-Time Neural Style Transfer for Videos, IEEE Conference on Computer Vision and Pattern Recognition (CVPR), 9 pages (2017).

Image Gradient, Wikipedia The Free Encyclopedia, retrieved from the internet URL: https://en.wikipedia.org/wiki/Image_gradient, accessed on Mar. 23, 2023, 3 pages.

International Search Report & Written Opinion dated Apr. 29, 2024 in Int'l PCT Patent Appl. Serial No. PCT/IB2024-051622 (011001).

International Search Report & Written Opinion dated May 29, 2024 in Int'l PCT Patent Appl. Serial No. PCT/IB2024-051624 (021001).

Ioffe, et al., Batch Normalization: Accelerating Deep Network Training by Reducing Internal Covariate Shift, retrieved from internet URL: https://arxiv.org/abs/1502.03167, 11 pages (2015).

Israel S.W., et al., "Improvement in Antenatal Diagnosis of Critical Congenital Heart Disease Implications for Postnatal Care and Screening," Fetal Diagnosis and Therapy, vol. 30(3):180-183, DOI:10.1159/000327148. (Apr. 2011).

Ji, et al., 3D Convolutional Neural Networks for Human Action Recognition, IEEE Transactions on Pattern Analysis and Machine Intelligence, 35(1), 8 pages (Jan. 2013).

Krizhevsky, et al., ImageNet Classification with Deep Convolutional Neural Networks, Communications of the ACM, 60(6):84-90 (Jun. 2017).

Kuehl, et al., Failure to Diagnose Congenital Heart Disease in Infancy, Pediatrics, 103(4):743-747 (Apr. 1999).

Landis B.J., et al., "Prenatal Diagnosis of Congenital Heart Disease and Birth Outcomes," Pediatric Cardiology, vol. 34(3):597-605, doi: 10.1007/s00246-012-0504-4. (Mar. 2013).

Levy, et al., Fetal Echocardiography: 5-4-3-2-1, The Levy-Stos Method, Gynecologie Obstetrique Pratique, No. 309 (Nov. 2018) (w-English Translation).

Levy, et al., Improved Prenatal Detection of Congenital Heart Disease in an Integrated Health Care System, Pediatr. Cardiol., 34:670-679 (Mar. 2013).

Liu, et al., Generalize Ultrasound Image Segmentation via Instant and Plug & Play Style Transfer, retrieved from internet URL: https://arxiv.org/abs/2101.03711, 5 pages (2021).

Liu, et al., Remove Appearance Shift for Ultrasound Image Segmentation via Fast and Universal Style Transfer, retrieved from internet URL: https://arxiv.org/abs/2002.05844, 6 pages (2020).

Mai C.T., et al., "National Population-based Estimates for Major Birth Defects, 2010-2014," Birth Defects Research, vol. 111(18):420-1435, doi:10.1002/bdr2.1589 (Nov. 2019).

Mamasoula C., et al., "Maternal age and the prevalence of congenital heart defects in Europe, 1995-2015: A register-based study," Birth Defects Research, vol. 115(6):583-594, Doi:10.1002/bdr2.2152. (Apr. 2023).

(56) References Cited

OTHER PUBLICATIONS

McMahon C.J., et al., "Paediatric and adult congenital cardiology education and training in Europe," Cardiol Young, vol. 32(12):1966-1983, DOI:10.1017/S104795112100528X. (Dec. 2022).

Moon-Grady A., et al., "Can a Complete Fetal Echocardiogram be Performed at 12 to 16 weeks' Gestation?" Journal of the American Society of Echocardiography: official publication of the American Society of Echocardiography, vol. 25(12):1342-1352, DOI:10.1016/j.echo.2012.09.003. (Dec. 2012).

Mozumdar N., et al., "Diagnostic Accuracy of Fetal Echocardiography in Congenital Heart Disease," Journal of the American Society of Echocardiography, vol. 33(11):1384-1390, DOI:10.1016/j.echo.2020.06.017. (Nov. 2020).

Nayak K., et al., "Evaluation of Fetal Echocardiography as a Routine Antenatal Screening Tool for Detection of Congenital Heart Disease," Cardiovascular Diagnosis and Therapy, vol. 6(1):44-49, doi:10.3978/j.issn.2223-3652.2015.12.01 (Feb. 2016).

Olney R.S., et al., "Detection of Critical Congenital Heart Defects: Review of Contributions from Prenatal and Newborn Screening," Seminars in Perinatology, vol. 39(3):230-237, doi:10.1053/j.semperi.2015.03.007 (Apr. 2015).

Optical flow, Wikipedia The Free Encyclopedia, retrieved from the internet URL: https://en.wikipedia.org/wiki/Optical_flow, accessed on Mar. 23, 2023, 6 pages.

Oster M.E., et al., "Temporal Trends in Survival Among Infants With Critical Congenital Heart Defects," Pediatrics, vol. 131(5):e1502-e1508, doi:10.1542/peds.2012-3435 (May 2013).

Ouyang, et al., Interpretable AI for Beat-to-Beat Cardiac Function Assessment, Stanford University, 23 pages (2019).

Pan, et al., An Improved Two-stream Inflated 3D ConvNet for Abnormal Behavior Detection, Intelligent Automation and Soft Computing, 29(3):673-688 (Jan. 2021).

Patra, et al., Multi-anatomy localization in fetal echocardiography videos, 2019 IEEE 16th International Symposium on Biomedical Imaging (ISBI 2019), pp. 1761-1764 (Apr. 2019).

Peiris V., et al., "Association of Socioeconomic Position and Medical Insurance With Fetal Diagnosis of Critical Congenital Heart Disease," Circulation. Cardiovascular quality and outcomes, vol. 2(4):354-360, DOI:10.1161/CIRCOUTCOMES.108.802868. (Jul. 2009).

Pinto N.M., et al., "Barriers to Prenatal Detection of Congenital Heart Disease: a Population-based Study," Ultrasound in Obstetrics & Gynecology, vol. 40(4):418-425, doi:10.1002/uog.10116 (Oct. 2012).

Pradat P., et al., "The Epidemiology of Cardiovascular Defects, Part I: A Study Based on Data from Three Large Registries of Congenital Malformations," Pediatr Cardiol, vol. 24(3):195-221, DOI:10.1007/s00246-002-9401-6. (May 2003).

Qiu, et al., Learning Spatio-Temporal Representation with Pseudo-3D Residual Networks, retrieved from the internet URL: https://arxiv.org/abs/1711.10305, 9 pages (2017).

Quartermain M.D., et al., "Variation in Prenatal Diagnosis of Congenital Heart Disease in Infants," Pediatrics, vol. 136(2):e378-e385, doi:10.1542/peds.2014-3783 (Aug. 2015).

Ruder, et al., Artistic Style Transfer for Videos and Spherical Images, International Journal of Computer Vision, 19 pages (2018).

Salomon L.J., et al., "Practice guidelines for performance of the routine mid-trimester fetal ultrasound scan," Ultrasound Obstet Gynecol, vol. 37(1):116-126, DOI:10.1002/uog.8831. (Jan. 2011).

Schneider C., et al., "Development of Z-scores for fetal cardiac dimensions from echocardiography," Ultrasound Obstet Gynecol, vol. 26(6):599-605, DOI:10.1002/uog.2597. (Nov. 2005).

Simonyan, Two-Stream Convolutional Network for Action Recognition in Videos, Visual Geometry Group, University of Oxford, 9 pages (2014).

Simonyan, Very Deep Convolutional Networks for Large-Scale Image Recognition, Visual Geometry Group, University of Oxford, 14 pages (2015).

Sonio Detect, FDA 510(k), K230365, Jul. 25, 2023, available at https://www.accessdata.fda.gov/cdrh_docs/pdf23/K230365.pdf.

Sonio Detect, User Manual, Nov. 2022, available at: https://sonio.ai/old/pt-br/sonioapp/dt-user-manual-pt-br/.

Stümpflen, Effect of detailed fetal echocardiography as part of routine prenatal ultrasonographic screening on detection of congenital heart disease, The Lancet, 348(9031):854-857 (Sep. 1996).

Suard C., et al., "Accuracy of prenatal screening for congenital heart disease in population: a retrospective study in Southern France," PLOS ONE, vol. 15(10):e0239476, 13 pages, DOI:10.1371/journal.pone.0239476. (Oct. 5, 2020).

Sun, et al., Human Action Recognition using Factorized Spatio-Temporal Convolutional Networks, retrieved from the internet URL: https://arxiv.org/abs/1510.00562, 9 pages (2015).

Sun H.Y., "Prenatal Diagnosis of Congenital Heart Defects: Echocardiography," Translational Pediatrics, vol. 10(8):2210-2224, doi: 10.21037/tp-20-164. (Aug. 2021).

Szegedy, et al., Going Deeper with Convolutions, 2015 IEEE Conference on Computer Vision and Pattern Recognition (CVPR), 9 pages (Jun. 2015).

Szegedy, Going Deeper with Convolutions, IEEE Conference on Computer Vision and Pattern Recognition (CVPR), 12 pages (2014).

Thomas, et al., Light-weight Spatio-Temporal Graphs for Segmentation and Ejection Fraction Prediction in Cardiac Ultrasound, *International Conference on Medical Image Computing and Computer-Assisted Intervention*, pp. 380-390 (Sep. 2022).

Tran, et al., A Closer Look at Spatiotemporal Convolutions for Action Recognition, retrieved from the internet URL: https://arxiv.org/abs/1711.11248, 10 pages (2018).

Tran, et al., Learning Spatiotemporal Features with 3D Convolutional Networks, IEEE International Conference on Computer Vision (ICCV), 16 pages (2015).

Tune Gaussian Mixture Models, retrieved from the internet URL: https://www.mathworks.com/help/stats/tune-gaussian-mixture-models.html, retrieved on Apr. 13, 2023, 7 pages.

Tworetzky W., et al., "Improved Surgical Outcome After Fetal Diagnosis of Hypoplastic Left Heart Syndrome," Circulation, vol. 103(9):1269-1273, DOI:10.1161/01.CIR.103.9.1269. (Mar. 6, 2001).

Ultrasound in Pregnancy. Practice Bulletin No. 175. American College of Obstetricians and Gynecologists, *Obstetrics& Gynecology*, 128 (6):1459-1460) (Dec. 2016).

Van Nisselrooij A.E.L., "Why Are Congenital Heart Defects Being Missed?" Ultrasound in Obstetrics & Gynecology, vol. 55(6):747-757, doi:10.1002/uog.20358 (Jun. 2020).

Varol, et al., Long-term Temporal Convolutions for Action Recognition, retrieved from the internet URL: https://arxiv.org/abs/1604.04494, 8 pages (2017).

Vivaaindrean, Detection of Robbery-Related Concepts Using Deep Learning, Final Year Project, UTAR, 56 pages (Jan. 2020).

Wang, et al., Actions ~ Transformations, retrieved from the internet URL: https://arxiv.org/abs/1512.00795, 10 pages (2016).

Wang, et al., Towards Good Practices for Very Deep Two-Stream ConvNets, retrieved from the internet URL: https://arxiv.org/abs/1507.02159, 5 pages (2015).

"WHO Recommendations on Antenatal Care for a Positive Pregnancy Experience," World Health Organization; 2016, Retrieved from internet URL:https://www.ncbi.nlm.nih.gov/books/NBK409108/ (Dec. 2022).

Wolfe, Deep Learning on Video (Part One): The Early Days, retrieved from the internet URL: https://towardsdatascience.com/deep-learning-on-video-part-one-the-early-days-8a3632ed47d4, 13 pages (2021).

Xie, et al., Rethinking Spatiotemporal Feature Learning: Speed-Accuracy Trade-offs in Video Classification, retrieved from the internet URL: https://arxiv.org/abs/1712.04851, 17 pages (2018).

\* cited by examiner

Normal 4 chamber view showing foramen ovale

View showing large atrioventricular defect

SYSTEMS AND METHODS FOR IMPROVING DETECTION OF FETAL CONGENITAL HEART DEFECTS

CROSS-REFERENCE TO RELATED APPLICATIONS

This application is a continuation-in-part of U.S. patent application Ser. No. 18/406,446, filed Jan. 8, 2024, now U.S. Pat. No. 12,082,969, which is a continuation-in-part of U.S. patent application Ser. No. 18/183,937, filed Mar. 14, 2023, now U.S. Pat. No. 11,869,188, which claims priority to EP patent application Ser. No. 23/305,235.6, filed Feb. 22, 2023, the entire contents of each of which are incorporated herein by reference. U.S. patent application Ser. No. 18/406,446, filed Jan. 8, 2024, now U.S. Pat. No. 12,082,969, also claims priority to U.S. Provisional Application No. 63/584,117, filed Sep. 20, 2023, the entire contents of which are incorporated herein by reference.

FIELD OF USE

The present invention is directed to systems and methods for improving detection of fetal congenital heart defects during and after ultrasound examination by using machine learning algorithms to ensure creation of a complete dataset, conduct preliminary review of the completed dataset, and determine datasets to be designated for expert review.

BACKGROUND

Congenital heart disease (CHD) is the most common birth defect with a prevalence of about 0.8-1% among all births. As of 2014, in the United States, CHD accounts for 4% of neonatal deaths, and for 30% to 50% of deaths related to congenital anomalies. A study by Nayak, et al. entitled "Evaluation of fetal echocardiography as a routine antenatal screening tool for detection of congenital heart disease," Cardiovasc. Diagn. Ther. 6, 44-49 (2016) demonstrated that 92% of CHD occurred in pregnancy defined as "low risk." Stümpflen, et al., in a study entitled "Effect of detailed fetal echocardiography as part of routine prenatal ultrasonographic screening on detection of congenital heart disease," The Lancet 348, 854-857 (1996) observed that most CHD are identified during the second trimester of pregnancy screening exam, supporting the need for a universal fetal heart screening exam during the second trimester of the pregnancy.

CHD is often asymptomatic in fetal life but causes substantial morbidity and mortality after birth. In addition to adverse cardiac outcomes, CHD is associated with an increased risk for adverse neurodevelopmental outcomes, associated with factors such as associated chromosomal abnormalities, syndromes, postnatal cardiac dysfunction, and in utero hemodynamic abnormalities. Critical CHD (see Table 1), defined as requiring surgery or catheter-based intervention in the first year of life, accounts for approximately 25 percent of all CHD. See, Oster, M. E. et al., "Temporal trends in survival among infants with critical congenital heart defects," Pediatrics 131, e1502-1508 (2013). In infants with critical cardiac lesions, the risk of morbidity and mortality increases when there is a delay in diagnosis and timely referral to a tertiary center with expertise in treating these patients. See Kuehl, K. S., et al. "Failure to Diagnose Congenital Heart Disease in Infancy," Pediatrics, 103:743-7 (1999): Eckersley, L., et al., "Timing of diagnosis affects mortality in critical congenital heart disease," Arch. Dis. Child. 101, 516-520 (2016).

TABLE 1

| Critical Congenital Heart Defects | Prevalence | Prenatal diagnosis (%) (based on ultrasound) |
|---|---|---|
| Coarctation of the aorta (COA) | 4 per 10 000 birth | 11% to 22% |
| Atrioventricular septal defect | 3.8 per 10 000 live birth | 40.8% to 66% |
| Conotruncal lesions | up to 20% of CHD detected prenatally | 24% to 26% |
| Transposition of the great arteries (TGA) | 3.7 per 10 000 live birth | 14% to 19% |
| Total anomalous pulmonary venous connection (TAPVC) | 1.3 per 10 000 live birth | 0% to 9.1% |
| Univentricular heart | 1.1 per 10 000 | 56% to 85% |
| Hypoplastic left heart syndrome (HLHS) | 2.7 per 10 000 | 56% to 83% |
| Valvular stenosis | Aortic valve stenosis: 1.1 per 10 000 Pulmonary valve stenosis: 1.5 per 10 000 | Aortic stenosis: 8.5% to 25.5% Pulmonary stenosis: 37% to 44% |

Compared to postnatal diagnosis, fetal diagnosis can dramatically improve neonatal outcomes by anticipating delivery care, surgical and/or early interventional planning and in some cases, considering in utero therapies. Further, accurate antenatal diagnosis allows the parents to make an informed decision regarding the continuation of pregnancy.

Distinguishing normal fetal hearts from those exhibiting complex forms of CHD typically involves an initial screening exam performed by physicians, nurse practitioners, physician assistants, ultrasound technicians, and other providers trained in diagnostic obstetric ultrasonography. Licensed medical providers who meet the training specialty guidelines are responsible for the interpretation of the ultrasound examination. Further examination via fetal echocardiography is warranted if the ultrasound is abnormal for confirmation and diagnosis refinement. Further examination may also be warranted under circumstances such as a family history of congenital heart defect, presence of maternal diabetes, or use of in vitro fertilization. Only well-trained and/or experienced pediatric cardiologists, maternal-fetal medicine specialists, obstetricians, or radiologists who have acquired the appropriate knowledge base and skills supervise and perform such fetal echocardiograms. Low sensitivity in this task can limit palliation options, worsen postnatal outcomes and hamper research on in utero therapies, while low specificity can cause unnecessary additional testing and referrals.

The World Health Organization (WHO) recommends that all pregnant women have one ultrasound scan before 24 weeks of pregnancy to estimate gestational age (GA), assess placental placement, determine single or multiple pregnancies, increase fetal abnormality detection, and improve pregnancy outcomes. WHO Recommendations on Antenatal Care for a Positive Pregnancy Experience (World Health Organization, 2016).

In 2013 and 2018, both the American Institute of Ultrasound in Medicine (AIUM) and the International Society of Ultrasound in Obstetrics and Gynecology (ISUOG) changed their practice guidelines for fetal heart screening of mid-gestation fetuses. See, Carvalho et al., "ISUOG Practice Guidelines (updated): sonographic screening examination of the fetal heart: ISUOG Guidelines," Ultrasound Obstet. Gynecol. 41, 348-359 (2013); "AIUM-ACR-ACOG- SMFM-SRU Practice Parameter for the Performance of Standard Diagnostic Obstetric Ultrasound Examinations," J. Ultrasound Med. 37, E13-E24 (2018). These updated guidelines specified a minimum of three views: the four-chamber view (4C) and views of the left (LVOT) and right (RVOT) ventricular outflow tracts (2, 3). Unfortunately, several heart malformations are not well detected prenatally with this approach. While the three-vessel (3V) and three-vessels-and-trachea (3VT) views are not mandatory in the AIUM and ISUOG practice guidelines, both guidelines state that these views are desirable and should be attempted as part of routine screening. See Table 2. Many groups already perform additional views during routine screening and report higher fetal heart malformation detection rates, of 62-87.5%, compared with 40-74% using the recommended three views, as described in "Committee on Practice Bulletins—Obstetrics and the American Institute of Ultrasound in Medicine, Practice Bulletin No. 175: Ultrasound in Pregnancy," Obstet. Gynecol. 128, e241-e256 (2016).

TABLE 2

| | |
|---|---|
| Transverse abdominal view | Transverse abdominal view showing the fetal stomach (St), cross-section of the descending aorta (dAo), spine (Sp) and liver (Li). |
| Four-chamber view (4C) | 4C view showing the right and left ventricles (RV, LV) and atria (RA, LA), foramen ovale (FO) and pulmonary veins (PV) to the right and the left of the descending aorta (dAo). |
| Left ventricular outflow tract view (LVOT) | LVOT view showing the aortic root (Ao), LV, RV, LA and RA and a cross-section of the dAo. |
| Right ventricular outflow tract view (RVOT) | RVOT view showing the main pulmonary artery (MPA) and the bifurcation into the right (RPA) and left (LPA) pulmonary arteries and cross-sections of the ascending aorta (Ao) and descending aorta (dAo). |

Some critical CHD are more amenable to visualization through ultrasound screening during the pregnancy than others. Using 1997-2007 data from the Utah Birth Defect Network, Pinto et al., in "Barriers to prenatal detection of congenital heart disease: a population-based study," Ultrasound Obstet. Gynecol. Off. J. Int. Soc. Ultrasound Obstet. Gynecol. 40, 418-425 (2012), observed that the defects most likely to be detected prenatally included those with abnormal four-chamber views, while defects exhibiting abnormal outflow tracts were much less likely to be detected prenatally. In a study of members of a large health maintenance organization (HMO) in California from 2005 to 2010, Levy et al., in "Improved prenatal detection of congenital heart disease in an integrated health care system," Pediatr. Cardiol. 34, 670-679 (2013), showed that women who received care from HMO clinics that had instituted a policy to examine outflow tracts during prenatal ultrasound had much higher prenatal diagnosis rates (59%) compared to HMO clinics that had not instituted such a policy (28%).

In current triaging workflows, a patient typically presents at a first point of care (OB-Gyn, Midwife or radiologist), where an assessment of the fetus is performed, e.g., via a fetal ultrasound screening performed by the healthcare professional or by a sonographer. The image data is interpreted in real time by a first line practitioner during the ultrasound exam or off line, after the exam has been performed. The report is generated by the first line practitioner and might be pre-filled in by the sonographer. If a congenital heart defect is suspected, the patient is referred to a specialist who will review the report, and perform a specific exam (echocardiography, genetic test) intended to confirm the presence or absence of the potential congenital defect. Depending upon the outcome of that further exam or test, a decision is made regarding treatment and/or transfer of the patient to a follow-up point of care.

Drawbacks to previously-known CHD screening workflow are numerous, and generally include: inaccuracy and low specificity caused by improper examination technique, time pressure, obesity of the mother, and simple misdiagnosis. In particular, CHD detection during a second trimester ultrasound exam is often as low as 30%. Specificity also is suboptimal, as low as 40-50% due to a lack of skill in adapting ultrasound images (i.e., ultrasound operator lacks the skill needed to obtain data from which a correct diagnosis can be made, resulting in about 49% of the misdiagnoses; lack of experience in formulating an accurate diagnosis (i.e., the images obtained are sufficient and the prenatal pathology is visible, but not recognized by the operator, resulting in about 31% of the misdiagnoses; the pathologies cannot be detected because they are not visible on the ultrasound images, accounting for about 20% of missed diagnoses. Time pressures associated with achieving adequate patient throughput in the clinical setting can exacerbate the foregoing issues, especially when transfer of a patient to a specialist is required.

While some efforts have been made to improve CHD detection during routine prenatal ultrasound examination, much is left to be done. For example, there is considerable guidance available to ultrasound technicians describing how to obtain a complete, high diagnostic quality dataset of images during an examination, and how to confirm the presence of cardiac structure in real time during an examination. For example, U.S. Pat. No. 7,672,491 to Krishnan et al. describes a system for evaluating the diagnostic quality of images acquired during an ultrasound examination that uses machine learning to compare the acquired images to expected images.

As discussed above, the ISUOG Practice Guidelines, published in *Ultrasound Obstet. Gynecol.* 2013; 41:348-359 suggests five axial locations that should be imaged during a routine fetal heart ultrasound examination, as well as the principal organs and vessels and orientations of each that should be confirmed at each location. European Patent Application Publication EP 3964136 to Voznyuk et al. describes a machine learning system that analyzes ultrasound images generated during an examination, uses a first convolutional neural network (CNN) to compare acquired images to views required by those guidelines, and a second CNN to analyze the images to identify potential abnormalities.

U.S. Patent Application Publication No. US 2021/0345987 to Ciofolo-Veit et al. describes an ultrasound imaging system that uses machine learning algorithms to analyze acquired images to detect anomalous features, and if an anomalous feature is detected, uses machine learning algorithms to determine and display other previously-acquired ultrasound images that provide complementary views of the potential anomalous feature to permit improved diagnosis.

In addition, a fetal ultrasound screening examination typically generates thousands of image frames spanning multiple structures per single video "sweep," so the diagnostic frames of interest for CHD may be only a handful and thus are easily missed. Moreover, the prevalence of CHD in the population (~0.8-1%) is low enough that non-experts see it only rarely and may discount or overlook abnormal images. Together, these factors make CHD detection one of the most difficult diagnostic challenges in ultrasound, with a dramatic impact on post-natal outcomes and quality of life.

In view of the foregoing, it would be desirable to provide methods and apparatus for triaging prenatal ultrasound scanning to improve accuracy of congenital defect detection, and subsequent management.

It further would be desirable to provide a machine-learning enabled system for pre-natal fetal ultrasound configured to review recorded ultrasound video and to identify images from the video that correspond to the views recommended by the guidelines.

It still further would be desirable to provide methods and systems for conducting prenatal ultrasound examinations that assist the sonographer in collecting a high-quality dataset in accordance with applicable guidelines, assist the interpreting physician and/or technician in identifying potential abnormalities in the acquired data, and moreover, in real time guides the sonographer to acquire additional views to augment the image dataset, e.g., to facilitate specialist review.

It still further would be desirable to provide methods and systems for objectively evaluating the performance of the sonographer over multiple exams.

SUMMARY

The present invention is directed to systems and methods for conducting fetal ultrasound examinations that aids in the detection of critical heart defects during a second semester ultrasound exam. The inventive systems and methods help trained and qualified physicians to interpret ultrasound recording motion video clips by analyzing video clips and identifying a risk of one or more abnormalities of the fetal anatomy. For example, the systems and methods of the present invention may assist in detecting and identifying morphological abnormalities that might be indicative of critical CHDs.

In one embodiment, the systems and methods are embodied in a computer assisted diagnostic aid for use in two-dimensional prenatal ultrasound exams of fetuses, such as usually performed during the second trimester of pregnancy. Machine learning algorithms are employed to assist users with the identification and interpretation of standard views in fetal cardiac ultrasound motion video clips. In particular, the inventive systems and methods are embodied in software that may be executed to support identification of critical CHDs. In addition, information generated during the machine learning augmented analyses may be stored for later referral to an expert (e.g., specialist) to assist further diagnosis and treatment planning.

In a preferred embodiment, the inventive system employs two components: a user interface component that provides a clinician tools to analyze and review fetal ultrasound images and ultrasound motion video clips, and a machine learning interpretative component that receives ultrasound motion video clips and images from a conventional fetal ultrasound screening system, identifies images within the motion video clips that correspond to fetal ultrasound screening guidelines. The interpretative component also analyzes the identified images to detect and identify the presence of morphological abnormalities, and provides that information to the user interface component to highlight such abnormalities for the clinician's review. The interpretative component may be executed partially or fully on a local computer workstation in real-time. Alternatively, the interpretative component may reside on a cloud-based server and interact with the user interface component via a secure connection on a local or wide area network, such as the Internet.

In accordance with another aspect of the invention, the methods and systems provide a consistent process to ensure that all views suggested by the practice guidelines for fetal exams are acquired. In particular, if the machine-learning based review of the motion video clips from the fetal ultrasound scan does not identify an image frame determined as appropriate for review, the system will flag that view as being unavailable or of inadequate quality to permit analysis for abnormality detection, the user interface will direct the clinician to re-perform the ultrasound scan to acquire the missing data. The new motion video clip then is transmitted to the interpretive component for analysis and a supplemental analysis will be returned to the user interface for presentation to the clinician.

In accordance with another aspect of the invention, the analysis results returned to the user interface component may be displayed and further annotated by the clinician to include additional graphical indicia or textual remarks. The resulting analysis results and annotations may be stored for later referral to an expert to develop a plan for further diagnosis or treatment.

In accordance with another aspect of the invention, analysis and/or results, including detected morphological abnormalities, may be used to generate a report. The report may be automatically populated with entries for each standard view using frames of video clips, which may include bounding box overlays. Information about the view may be included in the report to add context to the images.

In accordance with another aspect of the invention, the system may recommend a referral to a clinician and/or expert. In accordance with another aspect of the invention, the system may perform an objective evaluation of the technician that performed the imaging (e.g., the sonographer). In accordance with another aspect of the invention, the system may automatically organize the results with the most relevant information appearing first or otherwise most prominently. Additionally, or alternatively, the results may be organized by patient in order of severity.

In another embodiment, systems and computer implemented methods for analysis of fetal ultrasound images are provided. The systems and methods may include receiving a plurality of sets of image data generated by an ultrasound system during a fetal ultrasound examination, each set of image data of the plurality of sets of image data including a plurality of frames; analyzing a set of image data of the plurality of sets of image data to automatically determine that one or more frames of the set of image data corresponds to a standard view of a plurality of standard views; analyzing the set of image data to automatically determine that the one or more frames is indicative of a first morphological abnormality of a plurality of morphological abnormalities; generating a user interface for display, wherein the user interface includes: an image data viewer adapted to visually present the set of image data; a standard view indicator corresponding to the set of image data presented on the image data viewer and visually indicating whether each standard view of the plurality of standard views is present in the set of image data; and a morphological anomaly indicator corresponding to the set of image data presented on the image data viewer and visually indicating whether each morphological abnormality of the plurality of morphological abnormalities is present in the set of image data, wherein the standard view indicator indicates that a first standard view is present in the set of image data and the morphological anomaly view indicator indicates a first morphological abnormality is present when the image data viewer visually presents the set of image data.

The user interface may be generated on a display of the ultrasound system and/or generated on a display of a health care provider device. The standard view indicator may include a plurality of color indicators each corresponding to one of the plurality of standard views, each color indicator of the plurality of color indicators adapted to present a first color when a respective standard view of the plurality of standard views is present in the set of image data and a second color when the respective standard view of the plurality standard views is not present in the set of image data. The morphological anomaly indicator may include a plurality of color indicators each corresponding to one of the plurality of morphological anomalies, each color indicator of the plurality of color indicators adapted to present a first color when a respective morphological abnormality of the plurality of morphological abnormalities is present in the set of image data and a second color when the respective morphological abnormality of the plurality of morphological abnormalities is not present in the set of image data. Each color indicator of the plurality of color indicators may be further adapted to present a third color indicative that a presence of the respective morphological abnormality of the plurality of morphological abnormalities in the set of image data is inconclusive In another embodiment, a system for analysis of fetal ultrasound images is included. The system may include memory configured to store computer-executable instructions, and at least one computer processor configured to access memory and execute the computer-executable instructions to receive image data corresponding to data generated by an ultrasound system, the image data including a plurality of frames forming one or more video clip and showing a portion of fetal anatomy, determine a machine learning model including one or more neural networks trained to analyze the one or more video clip and generate outputs indicative of one or more of contours or coordinates corresponding to anatomy, analyze the image data using the machine learning model to generate at least one output, the at least one output indicative of at least one of first contours or first coordinates corresponding to the portion of fetal anatomy, determine a first value corresponding to the fetal anatomy and based on the at least one output, determine, based on the first value, an increased likelihood of a presence of a morphological abnormality in the fetal anatomy as compared to a default likelihood corresponding to the morphological abnormality, the morphological abnormality associated with a threshold value, generate an adjusted threshold value for the morphological abnormality based on the first value corresponding to the increased likelihood of the presence of a morphological abnormality, and replace a default threshold value associated with the morphological abnormality with the adjusted threshold value.

The at least one computer processor is further configured to access memory and execute the computer-executable instructions to: compare the first value to a first threshold value, and determine the first value does not satisfy a first threshold value. The at least one computer processor may be further configured to access memory and execute the computer-executable instructions to determine an increased likelihood of the presence of the morphological abnormality is based on the first value not satisfying the first threshold value. The at least one computer processor may be further configured to access memory and execute the computer-executable instructions to determine a score indicative of a difference between the first value and a default value corresponding to one or more patients different than the patient, compare the score to a first threshold value, and determine the score does not satisfy a first threshold value.

Determining the increased likelihood of the presence of the morphological abnormality may be based on the score not satisfying the first threshold value. The first value corresponds to a length, volume, or area of a feature of the fetal anatomy. The portion of anatomy may be a portion of cardiovascular anatomy. The at least one output may be indicative of a second value different than a first value, the second value corresponding to a second length, volume or area of a feature of the fetal anatomy. The at least one computer processor may be further configured to access memory and execute the computer-executable instructions to: determine that the second value does not satisfy the adjusted threshold value, and determine that the morphological abnormality corresponding to the adjusted threshold value is present based on the second value not satisfying the adjusted threshold value. The morphological abnormality may be one of enlarged cardiothoracic ratio, right ventricular to left ventricular size discrepancy, tricuspid valve to mitral valve annular size discrepancy, cardiac axis deviation, pulmonary valve to aortic valve annular size discrepancy, overriding artery, septal defect at a cardiac crux, or abnormal relationship of outflow tracts.

In another embodiment, a computer implemented method for analysis of fetal ultrasound images corresponding to a patient is provided. The computer implemented method may include receiving image data corresponding to data generated by an ultrasound system, the image data including a plurality of frames forming one or more video clip and showing a portion of fetal anatomy, determining a machine learning model including one or more neural networks trained to analyze the one or more video clip and generate outputs indicative one or more of contours or coordinates corresponding to anatomy, analyzing the image data using the machine learning model to generate at least one output, the at least one output indicative of one or more of first contours or first coordinates corresponding to the portion of fetal anatomy, determining a first value of the fetal anatomy based on the at least one output, determining, based on the first value, an increased likelihood of a presence of a morphological abnormality in the fetal anatomy as compared to a default likelihood corresponding to the morphological abnormality, the morphological abnormality associated with a threshold value, generating an adjusted threshold value for the morphological abnormality based on the first value corresponding to the increased likelihood of the presence of a morphological abnormality, and replacing a default threshold value associated with the morphological abnormality with the adjusted threshold value.

The computer implemented may further include comparing the first value to a first threshold value, and determining the first value does not satisfy a first threshold value. Determining an increased likelihood of the presence of the morphological abnormality may be based on the first value not satisfying the first threshold value. The computer implemented method may further include determining a score indicative of a difference between the first value and a default value corresponding to one or more patients different than the patient, comparing the score to a first threshold value, and determining the score does not satisfy a first threshold value. Determining the increased likelihood of the presence of the morphological abnormality may be based on the score not satisfying the first threshold value. The first value may correspond to a length, volume, or area of a feature of the fetal anatomy. The portion of anatomy may be a portion of cardiovascular anatomy. The at least one output is indicative of a second value different than a first value, the second value corresponding to a second length, volume or area of a feature of the fetal anatomy.

The computer implemented method may further include determining that the second value does not satisfy the adjusted threshold value and determining that the morphological abnormality corresponding to the adjusted threshold value is present based on the second value not satisfying the adjusted threshold value. The morphological abnormality may be one of enlarged cardiothoracic ratio, right ventricular to left ventricular size discrepancy, tricuspid valve to mitral valve annular size discrepancy, cardiac axis deviation, and pulmonary valve to aortic valve annular size discrepancy, overriding artery, septal defect at a cardiac crux, or abnormal relationship of outflow tracts.

In another embodiment, a computer implemented method for analysis of fetal ultrasound images corresponding to a patient is provided. The computer implemented method may include: receiving image data corresponding to data generated by an ultrasound system, the image data including a plurality of frames forming one or more video clip and showing a portion of fetal anatomy, analyzing the image data using a classification model including a first neural network to generate a first output, the classification neural network adapted to extract features from the plurality of frames and generate the first output indicative of a likelihood of a presence of a first morphological abnormality, analyzing the image data using a keypoint detection model including a second neural network to generate a second output, the keypoint detection neural network adapted to extract features from the plurality of frames, extract feature maps from the plurality of frames, and generate the second output indicative of coordinates of a plurality of anatomical features corresponding to the portion of the fetal anatomy, analyzing the image data using a segmentation model including a third neural network to generate a third output, the segmentation neural network adapted to extract features from the plurality of frames, extract feature maps from the plurality of frames, and generate the third output indicative of contours of a plurality of anatomical features corresponding to the portion of the fetal anatomy, and determining a presence of at least one abnormality corresponding to the portion of fetal anatomy based on one or more of the first output, the second output, or the third output.

The first morphological abnormality may be one of overriding artery, septal defect at the cardiac crux, or abnormal relationship of the outflow tracts. The computer implemented method may further include determining one of the following based on the second output: a location of one or more of a tricuspid valve, a mitral valve, a pulmonary valve, an aortic valve, an apex of a heart, a long axis of a heart, or an anteroposterior axis of a chest. The computer implemented method may further include calculating one or more of the following based the location of one or more of the tricuspid valve, the mitral valve, the pulmonary valve, or the aortic valve: tricuspid valve to mitral valve annular size discrepancy, pulmonary valve to aortic valve annular size discrepancy, and cardiac axis deviation. The computer implemented method may further include calculating one or more of the following based the location of one or more of the tricuspid valve, the mitral valve, the pulmonary valve, or the aortic valve: an enlarged cardiothoracic ratio or a right ventricular to left ventricular size discrepancy. The computer implemented method may further include determining, based on the third output, a contour of one or more of a left ventricle, a right ventricle, a heart, or a thorax.

The foregoing summary is illustrative only and is not intended to be in any way limiting. In addition to the illustrative aspects, embodiments, and features described above, further aspects, embodiments, and features will become apparent by reference to the following drawings and the detailed description.

BRIEF DESCRIPTION OF THE DRAWINGS

FIGS. 4A and 4B are exemplary images presented to a clinician via the user interface module after analysis results are returned from the interpretive module, in which FIG. 4A shows an image selected as corresponding to the four chambers view and FIG. 4B is a similar view for a different fetus including a bounding box identifying a large atrioventricular defect.

DETAILED DESCRIPTION OF THE INVENTION

Systems and methods are disclosed for conducting fetal ultrasound examinations that aid in the detection of critical heart defects during a fetal ultrasound exam, typically conducted during the second trimester. In particular, the inventive systems and methods assist trained and qualified physicians to interpret ultrasound recording motion video clips to assist in detecting and identifying morphological and flow abnormalities that may be indicative of critical CHDs. Table 3 provides an exemplary correspondence between representative CHDs, the views in which those CHDs usually appear, and the morphological abnormalities that typically can be identified in those views.

Figure 1A:
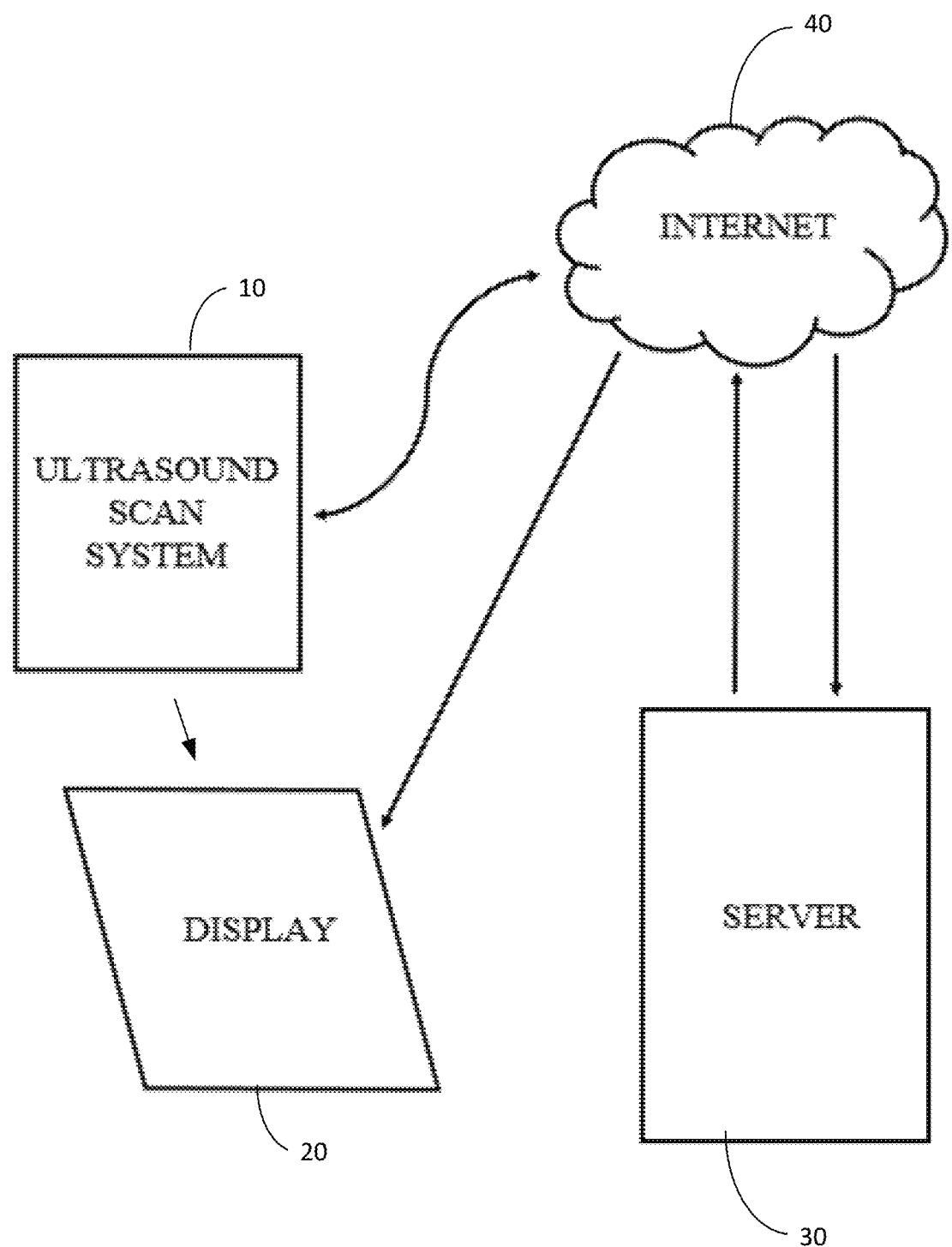
FIGS. 1A-1C are schematic views of an exemplary server-based and/or local models for implementing the methods and systems of the present invention.

In an exemplary system depicted in FIG. 1A, the system may include a conventional ultrasound system 10, display computer 20, and server system 30 that communicate with each other via wide area network 40, illustratively, the Internet or any other suitable network (e.g., local area network). In an embodiment, the systems and methods are embodied in a computer assisted diagnostic aid for use in two-dimensional fetal ultrasound exams, such as usually performed during the second trimester of pregnancy. Machine learning algorithms are employed to assist users with the identification and interpretation of standard views in fetal cardiac ultrasound motion video clips. While ultrasound systems are described throughout, it is understood that the same or a similar approach may be used with any other suitable medical imaging system (e.g., CT (computed tomography) scan, Magnetic resonance imaging (MRI), etc.).

In one embodiment, the inventive methods and systems employ two software components: a user interface component and an interpretative component. The user interface computer may be resident on display computer 20 and provide a clinician tools to analyze and review fetal ultrasound images and ultrasound motion video clips. The interpretative component may reside on server computer 30, receives ultrasound motion video clips and images from ultrasound system 10 or display computer 20, and uses machine learning algorithms to identify images within the motion video clips that correspond to fetal ultrasound screening guidelines. The interpretative component also analyses the identified images as well as any non-identified images (e.g., corresponding to non-standard or non-recommended views) to detect and identify the presence of morphological abnormalities, and provides that information to the user interface component to highlight such abnormalities for the clinician's review. In an alternative embodiment, the interpretive component may be executed partially or fully on a local computer workstation in real-time.

As is typical, ultrasound system 10 includes a handheld probe that a clinician moves across a patient's abdomen to generate motion video clips of the fetus during a pre-natal fetal examination, which clips may be transmitted to display computer 20 during the scanning process for storage and display on a display screen associated with display computer 20. The motion video clips generated during the examination may be any suitable period of time (e.g., series of still images, one second video clip, multi-second video clip, multiple minute video clip, etc.), and may be directly uploaded from ultrasound system 10 to server system 30 via wide area network 40 or any other suitable wireless technology, and/or may be transmitted by a user interface module executing on display computer 20.

Display computer 20 may be configured to display real-time video generated by ultrasound system 10, and in addition, is configured to display to the clinician analysis results generated by the interpretive component executing on server system 30. Display computer may include a display screen, storage, CPU, input devices (e.g., keyboard, mouse) and network interface circuitry for bi-directionally communicating with server system 30 via wide area network 40. In an embodiment, display computer 20 executes the user interface component of the invention, which accepts and stores physiologic information about the patient. Display computer 20 also receives and stores real-time ultrasound video from ultrasound system 10 and relays that image data, together with the patient's physiologic information, to the interpretative component that executes on server system 30.

Server system 30 includes the interpretive component of the inventive system, including machine learning algorithms for analyzing the motion video clips received from display computer 20 to compare the ultrasound video clips to a set of the preferred image templates that correspond to the fetal ultrasound examination guidelines. In an embodiment, the interpretive component may include image templates that correspond to each of the views recommended in the fetal heat ultrasound screening guidelines set forth in Table 2, including: (1) the transverse abdominal view; (2) the four chamber view (4C); (3) left ventricular outflow tract view (LVOT); (4) right ventricular outflow tract view (RVOT); (5) the three vessel view (3V) and (6) the three vessel and trachea view (3VT). The forgoing list is exemplary and non-limiting. Other standard views may include ductal arch view, bicaval view, abdominal situs view, and aortic arch view, for example. As described in further detail below, the interpretative component may employ machine learning to compare each frame of the input motion video clips to the foregoing view templates, and select one or more high quality image frames as corresponding to the selected template. If an abnormality is detected, an image frame showing the abnormality may be selected. The interpretative component may employ a machine learning model to analyze each of the image frames, selected as representative of the guideline views, and optionally other non-selected image frames, for the presence of the abnormalities known to be present in those image templates as set forth in Table 3.

For example, one the interpretive component has identified and selected an image frame from an uploaded motion video clip as representative of the 3VT view, the machine learning feature will analyze the selected image frame for features identified in Table 3 as being visible in the 3VT view: aorta greater than pulmonary artery, associated with coarctation of the aorta and conotruncal lesions; right aortic arch, associated with conotruncal lesions; abnormal vessel alignment, associated with transposition of the great arteries; and additional visible vessel, associated with anomalous pulmonary venous connection.

If the interpretative component of the system identifies one or more of the features described in Table 3 as being present in the selected image frame, the system further may create an overlap on the selected image that includes a bounding box that surrounds the detected abnormality and optionally, a textual label associated with the suspected defect. The selected image frames and analytical results then are transmitted back to display computer 20 for presentation to, and consideration by, the clinician. As clinicians often have multiple patients, the clinician may be sent or may otherwise be tasked with reviewing results from several patients. To facilitate efficient review by the clinician and/or expert, the system may automatically organize the results with the most relevant information, such as detected morphological abnormalities, appearing first or otherwise most prominently. Additionally, or alternatively, the results may be organized by patient in order of severity.

Display computer 20 may provide the ability to annotate the selected image frames with additional graphical or textual notes, which are then saved with the results for later recall during preparation of a documentary report concerning the fetal ultrasound examination.

If during analysis by the interpretative component no motion video clip image frame is identified as corresponding to a standard view template, or the identified image frame is adjudged to be of too poor quality to permit analysis for potential defects, that image template is identified as missing when the analysis results are transmitted back to display computer 20. In this case, the clinician may be prompted by display computer 20 to rescan the fetus to acquire the missing view, and that motion video clip may be resubmitted to the interpretative component for supplemental analysis.

The results of the supplemental analysis may then be sent back to display computer 20 for presentation to, and consideration by, the clinician.

Figure 1B:
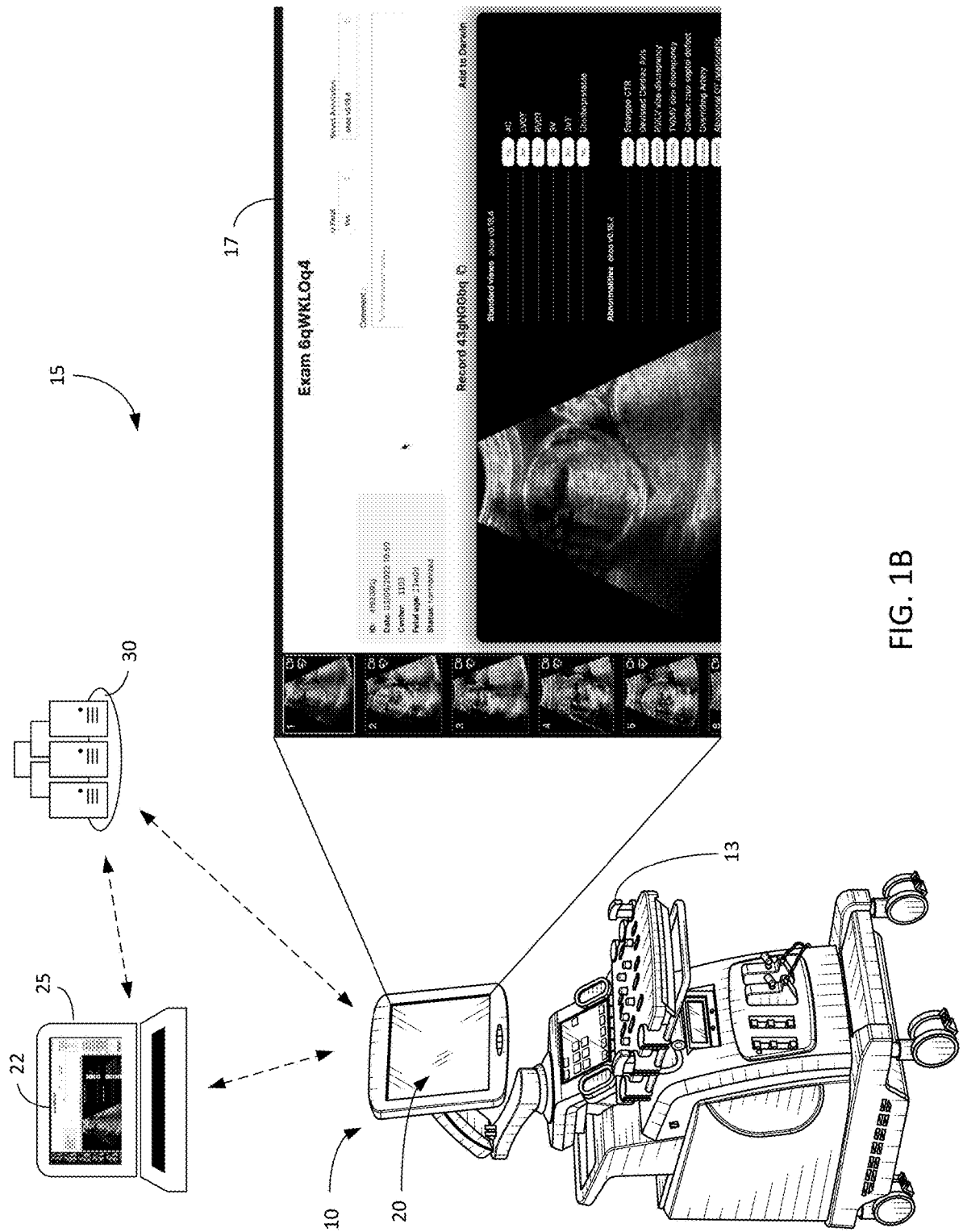

Referring now to FIG. 1B, the exemplary system of FIG. 1A is illustrated. System 15 may be the same as the system illustrated in FIG. 1A and may include ultrasound system 10, display computer 20, and server 30. As shown in FIG. 1B, ultrasound scan system 10 may be any suitable ultrasound scan system for performing fetal anatomic ultrasound examinations (e.g., second-trimester fetal anatomic ultrasound examinations between 18 and 24 weeks of gestation, first-trimester examinations, third-trimester fetal examinations, or otherwise), however, the inventive software/programming described herein is stored and executed on the controller of ultrasound scan system 10. In one example, ultrasound scan system 10 may be Samsung's WS80A ultrasound system, or any other suitable ultrasound scan system. Ultrasound scan system 10 may include ultrasound probes (e.g., probe 13), a display, one or more computers, inputs (e.g., keyboard, mouse, knobs, dials, switches, toggles, and the like), speakers, a microphone, and the like. System 15 may optionally also include healthcare provider device 25 which may include display 22.

Healthcare provider device 25 may be a standalone computer device which may display to healthcare provider (e.g., doctor, technician, specialist, etc.) analysis results generated by the interpretive component executing on server system 30. Display computer may include a display screen, storage, CPU, input devices (e.g., keyboard, mouse) and network interface circuitry for bi-directionally communicating with server system 30 and/or computer device 20 via any suitable wired or wireless connection. Display computer 20 and optionally healthcare provider device 25 may execute the user interface component of the invention. For example, display computer 20 and/or healthcare provider device 25 may display graphic user interface 17 which may be any graphic user interface described herein (e.g., graphic user interface 200 of FIGS. 8A-8C). Healthcare provider device 25 may communicate with server 30 and/or computer device 20 to provide input, comments, edits, and otherwise adjust or modify the graphic user interface.

Figure 1C:
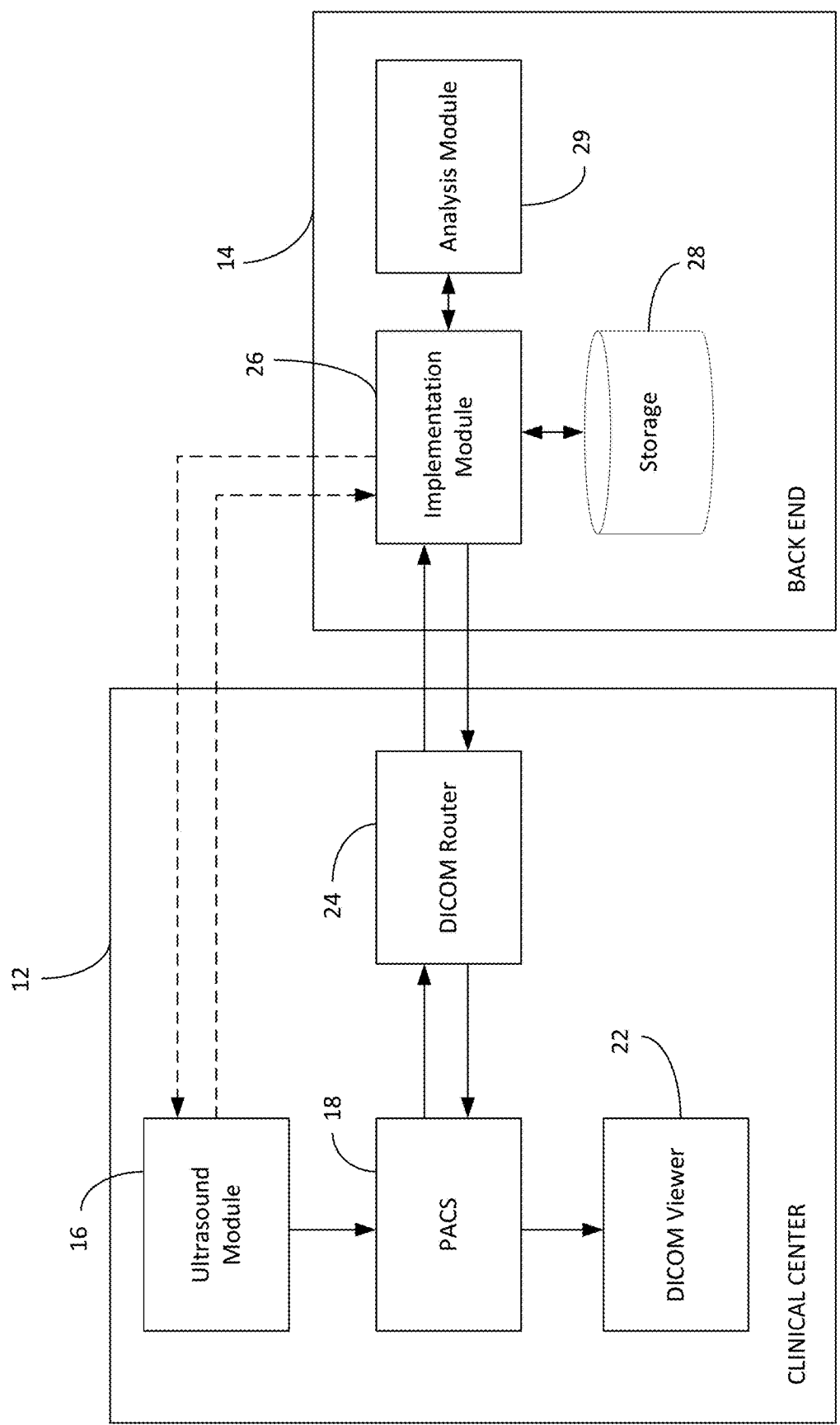

Referring now to FIG. 1C, a clinical workflow of the systems illustrated in FIGS. 1A-1B is illustrated. As shown in FIG. 1C, clinical center 12 may communicate with back end 14, which may be running on a server (e.g., server 30 of FIG. 1A). Clinical center 12 may include ultrasound module 16 which may run on the ultrasound scan device (e.g., ultrasound scan device 10 and/or display computer 20 of FIG. 1A), Picture Archiving and Communication (PACS) system 18, which may run on the ultrasound scan device or device located in the same building or campus as the ultrasound scan device and/or on a remote server, Digital Imaging and Communications in Medicine (DICOM) viewer 22, and DICOM router 24.

Ultrasound module 16 may generate, receive, obtain, and/or store ultrasound images (e.g., image data such as motion video clips and image frames). The image data may be communicated from ultrasound module 16 to PACS system 18. PACS system 18 may securely store image data received from ultrasound module 16. The image data saved in PACS system 18 may electronically label the record based on user selection input. Once the image data is saved and/or labeled in PACS system 18, DICOM router 24 may connect to PACS system 18 to retrieve the image data and may also connect to back-end 14, which may run on a server (e.g., server 30 of FIG. 1A). For example, DICOM router 24 may be connected to implementation module 26 and may send the image data to implementation module 26. In one example, DICOM router 24 may pseudonymize files so that only pseudonymized files are sent to the back end 14. For example, all patient information may be removed except for certain necessary variables (e.g. fetal age), and pseudonym identifiers may be added to the file for the exam and/or for each recording. Once DICOM router 24 receives outputs from back end 14, it may then perform re-identification, by replacing the pseudonym identifiers with the patient information. Implementation module 26 may upload the image data to storage 28. For example, storage 28 may store encrypted and otherwise secured image data.

Implementation module 26 may retrieve certain image data from storage 28 and may communicate such image data to analysis module 29. Analysis module 29 may process the image data (e.g., video clip) using machine learning algorithms to identify the presence of morphological abnormalities in the image data, as described in more detail herein with respect to FIGS. 3A and 3B. In one example, the outcomes and/or outputs of analysis module 29 may be stored in storage 28 as annotated DICOM files. The annotated DICOM files (e.g., indicating morphological anomalies) may be communicated back to DICOM router 24 and stored in PACS 18. Once stored in PACS 18, a healthcare provider (e.g., physician) using DICOM viewer 22 to access the annotated DICOM files from PACS 18 and view the annotated DICOM files (e.g., using a healthcare provider device).

Figure 2:
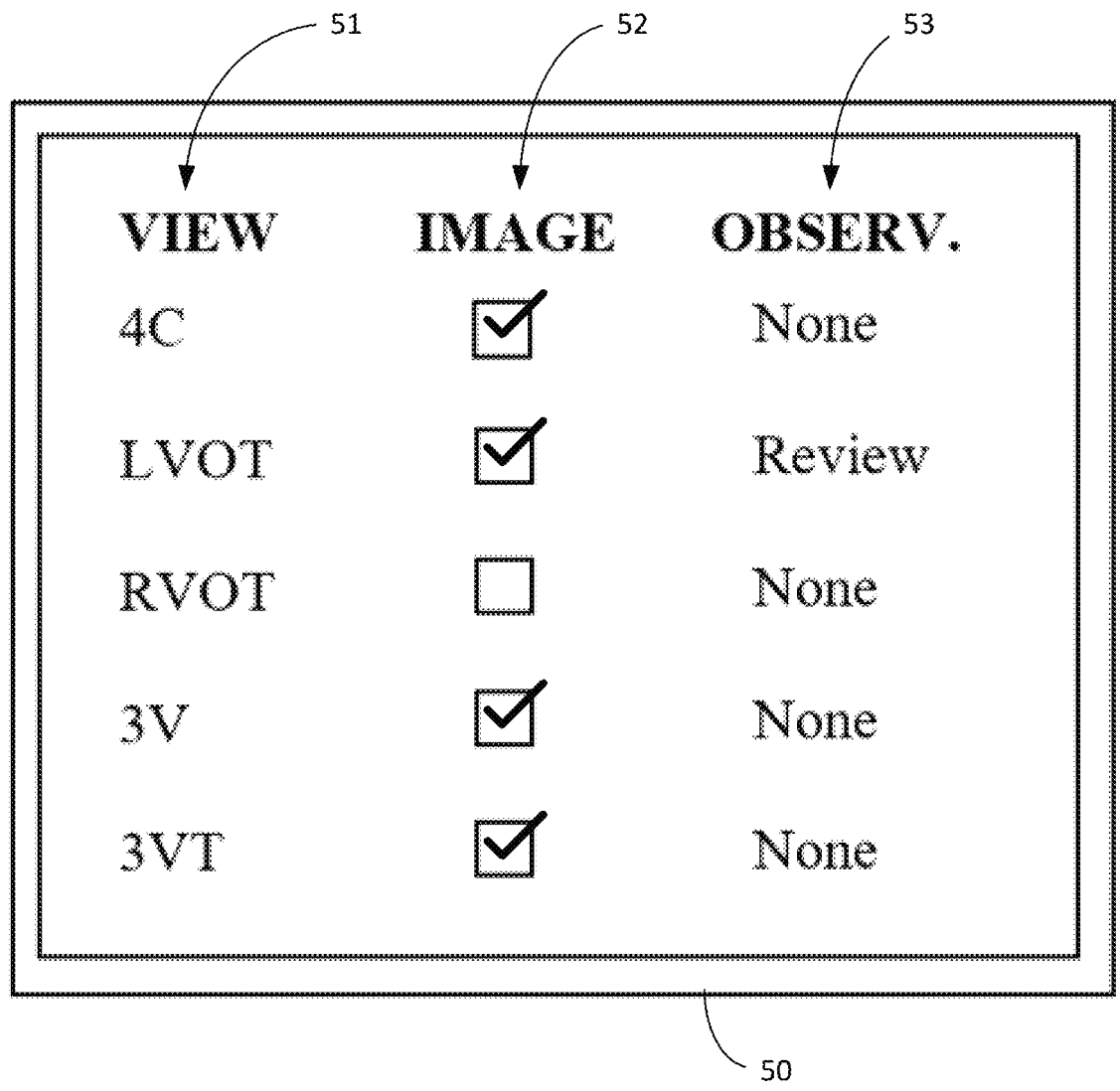
FIG. 2 is an exemplary screen display presented to the clinician showing the results returned to the user interface by the interpretive component.

Referring now to FIG. 2, an exemplary display suitable for summarizing the results returned to display computer 20 by the interpretative component residing on server system 30 is described. Display 50 includes three columns 51-53, which may include links that can be activated using the input device, e.g., a mouse, associated with display computer 20. Column 51, labeled "View," describes the standard guidelines views (e.g., 4C, LVOT, etc.). Column 52, labeled "Image," includes checkboxes indicating whether the interpretative component of the system has identified and selected an image frame as corresponding to the standard guidelines view. Column 53, labeled "Obser," denotes whether any observations, such as potential abnormalities, have been detected in a selected image frame.

Activating a link in the View column, column 51, such as by clicking on the view title with a mouse, will display an idealized generic image of the standard guideline view, such as those shown in Table 2. In column 52, the presence of a checkbox indicates that an image frame was selected by the interpretative component on server computer 30. Clicking on that checkbox will cause the display computer to display the raw image selected by the interpretative component. The absence of a checkbox in column 52 indicates that the interpretative component was unable to locate an image in the motion video clips suitable for analysis by the machine learning feature. Clicking on the empty checkbox, for example, for RVOT in FIG. 2, may be configured to display a prompt to the clinician to rescan a portion of the patient's abdomen to acquire a new motion video clip containing the desired view, which then may be sent to server computer 30 for supplemental analysis.

Column 53 may include textual descriptions for any observations noted by the interpretative component in the selected image frames. For example, in FIG. 2, column 53 presents the labels "None" for all views except the RVOT view. Because display 50 may be visible to the patient, column 53 may use neutral labeling, "Review," to indicate to the clinician that a potential abnormality was detected in that view, rather than a more descriptive label that could cause undue concern to the patient. In one embodiment, the textual indicators for each standard view may be clickable links. For example, clicking on a label that states "None" for the 4C, LVOT, 3V and 3VT views in FIG. 2 may display the image frame selected by the interpretative component along with labels that indicate where the interpretative component adjudged the anatomical landmarks to be located. On the other hand, clicking on the label "Review" for the RVOT view in FIG. 2 may display the selected image frame, labeled anatomical landmarks, and a bounding box surrounding the suspected abnormality, along with a textual description of the potential defect.

In a fetal ultrasound examination conducted in accordance with the principles of the present invention, following review of the real-time ultrasound motion video clips generated by the ultrasound scanner 10 as displayed on display computer 20, the clinician then may review the analysis results generated and returned by the interpretative component residing on server computer 30. In this manner, the clinician may review the contents of display 50 of FIG. 2, review the selected raw image data corresponding to each standard guideline view (by clicking on the checkboxes in column 52), and review the detailed machine learning analysis of that selected image frame by clicking on the labels in column 53. The clinician therefore may be able to corroborate his or her own observations during review of the real-time video clips or adjust his or her findings based on the machine learning analysis results. As noted above, display computer 20 may include the ability to open additional boxes associated with any of the image frames presented in column 53 to record and store additional findings for later recall in preparing a written or electronic report documenting the fetal ultrasound examination.

Figure 3A:
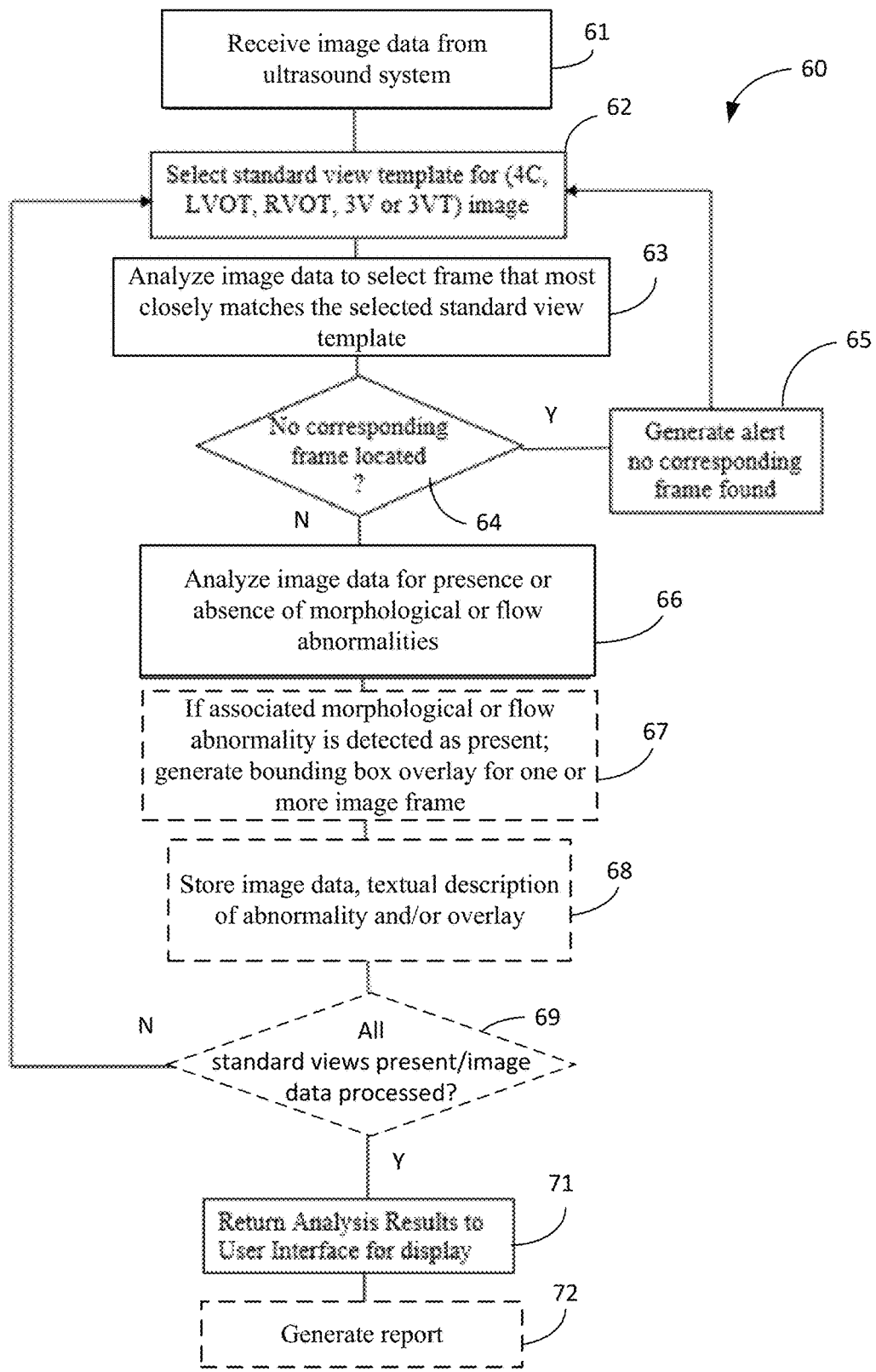
FIGS. 3A-3B are an exemplary flowchart and data flow showing the analysis process undertaken by the interpretive component to analyze motion video clips generated during a fetal ultrasound examination.

Turning now to FIG. 3A, exemplary flowchart 60 for the interpretative component of the analysis software is described. It is understood that the tasks and/or operations performed in flowchart 60 may be performed on a server (e.g., server 30 of FIG. 1), ultrasound scan system (e.g., ultrasound scan system 10 of FIG. 1), and/or display (e.g., display 20 of FIG. 1). At step 61, image data (e.g., motion video clips having a duration less than 1 second, between 1 second and one minute, or between 1 minute and one or more hours, image frames, and the like) are received from and/or determined by ultrasound system 10 or display computer 20. The image data may be any type of medical image such as, for example, greyscale ultrasound images, ultrasound images representing the intensity and/or direction of the flow (e.g., using Color Doppler, Power Doppler, etc.). At step 62, standard guideline view and/or a template corresponding to a standard guideline view is selected, e.g., 4C, LVOT, RVOT, 3V or 3VT. The template may consist of an idealized version of the images shown in Table 2 or other standard views or desirable views. At step 63, the received image data, which may be video image clips, is analyzed using a machine learning algorithm, e.g., convolutional neural network and/or deep neural network, to compare each frame (e.g., image frame) of the received motion video clip and/or pixels of the motion video clip to the standard template to determine which frame or frames best match the standard view guideline template. It is understood that a video clip, formed from a set of image frames and/or pixels, or individual image frames may be analyzed at step 63. The interpretative component also may analyze the selected image frame or frames to confirm that the image meets specified quality requirements for clarity. If no frame in the image data is determined to correspond to the standard view, at decision box 64, the process moves to step 65, where a flag is set indicating that no suitable image frame is available, and the process continues with selection of the next standard view template at step 62.

If the interpretative component adjudges that a corresponding frame is available in the received image data, the process moves to step 66, where the image data (e.g., selected image frames), and optionally non-selected image frames, are analyzed by another machine learning algorithm to detect the presence or absence of an abnormality associated with that image data (e.g., the image data in the standard view). For example, if the selected image frame corresponds to the 4C standard view template, the algorithm will analyze the selected frame for the presence of any of the defects and/or abnormalities listed in Table 3 for that standard view. If a defect is detected in the image data (e.g., the selected image frame), the algorithm may look at adjacent frames of the video clip to confirm the presence of the same defect.

Morphological abnormalities may include, in one example, overriding artery (e.g., artery going out of the left ventricle is positioned over a ventricular septal defect), septal defect at the cardiac crux (e.g., the septal defect located at the crux of the heart, either of the primum atrial septum or of the inlet ventricular septum), parallel great arteries, enlarged cardiothoracic ratio (e.g., ratio of the area of the heart to the thorax measured at the end of diastole above 0.33), right ventricular to left ventricular size discrepancy (e.g., ratio of the areas of the right and left ventricles at the end of diastole above 1.4 or below 0.5), tricuspid valve to mitral valve annular size discrepancy (e.g., ratio between the tricuspid and mitral valves at the end of diastole above 1.5 or below 0.65), pulmonary valve to aortic valve annular size discrepancy (e.g., ratio between the pulmonary and aortic valves at the end of systole above 1.6 or below 0.85), abnormal outflow tracts relationship (e.g., absence of the typical anterior-posterior cross-over pattern of the aorta and pulmonary artery), cardiac axis deviation (e.g., cardiac axis (angle between the line bisecting the thorax and the interventricular septum) below 25° or above 65°), abnormal pulmonary venous return, coarctation of the aorta, and mitral regurgitation, tricuspid regurgitation, pulmonary regurgitation, or aortic valve regurgitation. Alternatively, or additionally, any other morphological abnormalities may be detected step 66.

Additionally, or alternatively, image data (e.g., Doppler ultrasound image data such as color Doppler ultrasound image data and/or Power Doppler ultrasound image data) may be analyzed by a machine learning algorithm to detect the presence or absence of a blood flow abnormality. For example, video clips generated by Doppler ultrasound may show color patterns and/or changes indicative of abnormal blood flow. One or more frame from such color video clips may be analyzed by a machine learning algorithm trained to detect abnormal blood flow (e.g., abnormal blood flow at certain standard views (e.g., LVOT)) and may process color images from color video clips and generate an output indicative of normal or abnormal blood flow, or optionally an inconclusive finding. It may be desirable to train machine learning models to detect changes in patterns and other features indicative of blood flow to determine whether the flow is abnormal. Analysis of multiple sequential image frames may be necessary to determine whether the blood flow is abnormal. Analyzing blood flow may be helpful in determining if certain anatomy is functioning properly and/or determine if certain anatomy is properly connected (e.g., such anatomy may be too small to tell from greyscale ultrasound images alone). It will be understood by one of ordinary skill in the art that color video clips and images may be used to identify morphological abnormalities as well as blood flow abnormalities. For example, the color video clip may be analyzed by a machine learning algorithm and may generate an output indicative of a morphological abnormality due to blood flow found in regions of the heart not found in a properly functioning heart. In one example, using color Doppler ultrasound image data, the direction of blood flow may be determined. Using the direction of the blood flow as an input, a machine learning algorithm may detect a presence, absence, and/or inconclusiveness of a finding, such as one or more morphological defects (e.g., ventricular septal defect, atrial septal defect, abnormal pulmonary venous return, coarctation of the aorta, pulmonary valve atresia, or overriding artery).

In another example, blocks 62, 63 and 65 and decision 64 may be optional and block 66 may be initiated directly after block 61. In this example, all of the image data may be analyzed at block 66 to determine the presence or absence of morphological or flow abnormalities. For example, image data may include a one second video clip made up of multiple image frames and each image frame may be analyzed at block 66 to determine a presence or absence of morphological or flow abnormalities, or otherwise that such analysis is inconclusive.

At optional step 67, an overlay may be created for the selected image frame that includes graphical pointers to the detected anatomical landmarks, as well as a bounding box that surrounds the abnormality detected in the image frame. The overlay also may additionally or alternatively include textual information that describes the specific abnormality and/or the associated class of CHD, as set forth in Table 3. At step 68, the information generated by the interpretative component, i.e., the overlay and graphical/descriptive information is associated with the image data (e.g., selected image frame) and stored in server computer 30 for later transmission to display computer 20. At optional decision box 69, a determination is made whether all image data received at step 61 has been analyzed and/or if all standard views have been determined to be present. If not all standard views have been determined to be present and/or all image data received at step 61 has not been analyzed, the process may return to step 62, where the next standard view template is selected for analysis. Alternatively, if at decision box 69 is it determined that all standard views have been determined to be present and/or all image data has been analyzed, the process may move to step 71, where the results are returned to display computer 20 for presentation and review by the clinician. Alternatively, decision 69 may be optional and may be bypassed to initiate blocks 71 and/or 72. For example, a user may determine to return the analysis results to the user interface for display and/or generate a report even if all the standard views have not been determined to be present and/or all the image data has not been analyzed.

At optional step 72, the analysis and/or results may be used to generate a report. For example, the report may identify detected morphological and/or blood flow abnormalities and/or may include an entry for each standard view. Alternatively, only an entry for standard views that are determined to be present may be included in the report. For example, detected anomalies may include one or more of abnormal ventricular asymmetry, coarctation of the aorta, pulmonary or aortic valve stenosis, ventricular hypoplasia or univentricular heart and/or any other cardiovascular abnormality. The report may be prepopulated such that, for each standard view entry, a representation image may be selected. If a morphological and/or flow abnormality is detected, an image representative of the morphological and/or flow abnormality for a given standard view may be included in the report at the entry for the corresponding view. If a bounding box is generated for a given frame, such image with the bounding box overlay may be used in the report. Information about the view, the anatomy, any textual description of the detected morphological defect and/or abnormality and/or flow abnormality, and/or any other relevant information may additionally be included in the report to add context to the images and otherwise generate a more informative report. The resulting analysis, results, annotations, and/or report may be stored for later reference.

The images, image frames, video clips, analysis, results, annotations, and/or report may be shared with or otherwise made available to an expert or clinician (e.g., upon referral to an expert or clinician). Each type of morphological and/or flow abnormality may be associated with an expert or clinician and their contact information. If a morphological abnormality is detected at step 66, an expert or clinician corresponding to the morphological abnormality may optionally be recommended.

In addition to performing the steps 61-72 illustrated in FIG. 3A, the system may perform an objective evaluation of the exam, the images generated, and/or the technician that performed the imaging (e.g., the sonographer). The system may consider data such as the mean duration of the exam and/or image collection, the quality of the images acquired, the percentage of standard views for which a suitable image is acquired, and/or any other information indicative of the quality of the exam, the images and/or the sonographer. For example, a model trained to generate one or more quality values indicative of the quality of the exam and/or images may be used to process such data. The data may be determined over the course of several exams. For example, the percentage of standard views for which a suitable image is acquired for multiple exams by the same technician may be used to determine a quality value indicative of the rate at which a technician performs a complete exam.

Figure 3B:
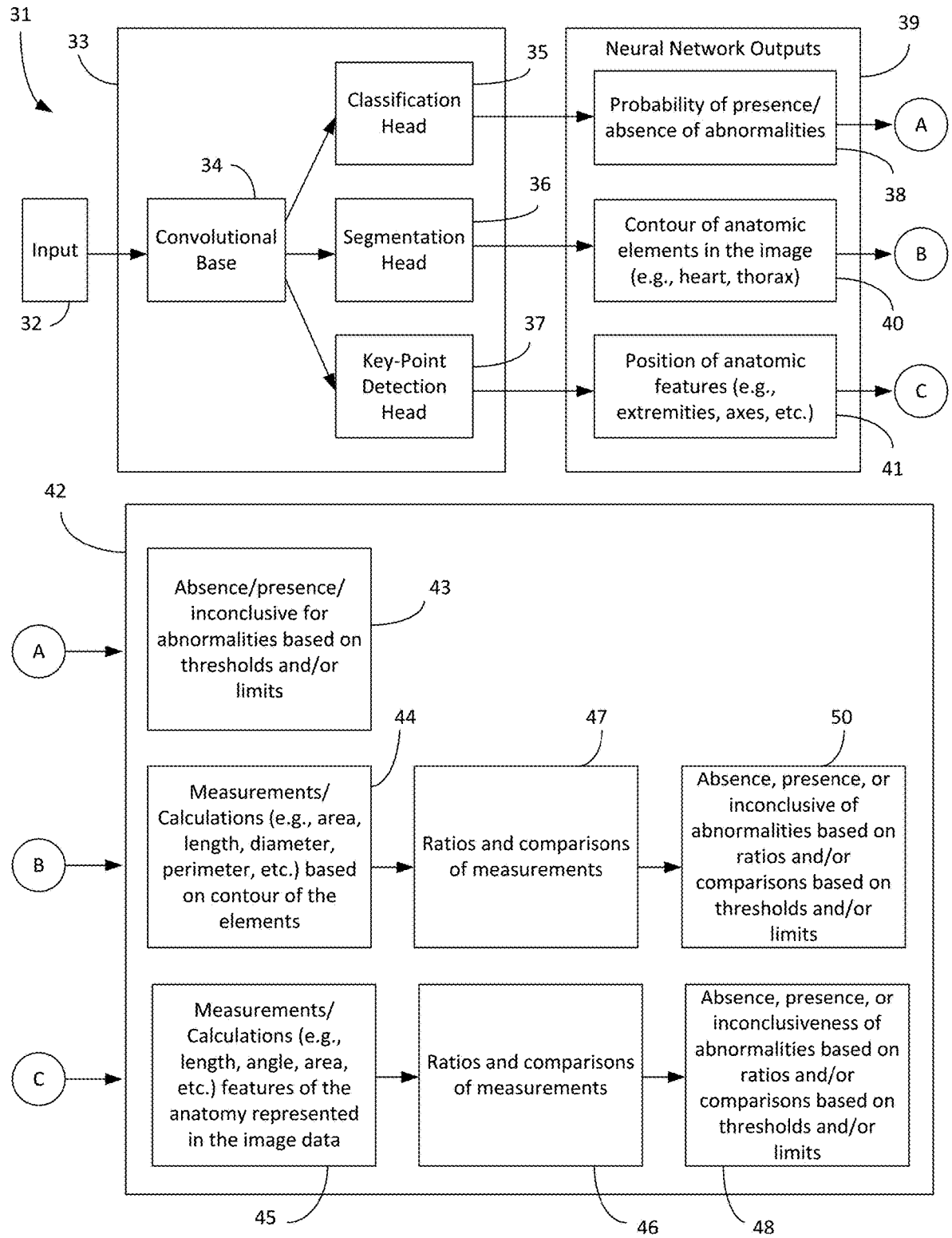

Turning now to FIG. 3B, neural network outputs and post processing steps of the analysis software is described. As shown in FIG. 3B, input 32 may be input into model 33 of analysis system 31. Model 33 may be one or more neural networks. Input 32 may be image data such as a motion video clip (e.g., one second video clip), image frame, and the like. In one example, input 32 may be raw digital data representing or forming the image data. Model 33 may include convolutional base 34, classification head 35, segmentation head 36, and key-point detection head 37. Convolutional base 34 may be a convolutional neural network (CNN) which may process input 32. Convolutional base 34 may include classification head 35, segmentation head 36, and key-point detection head 37.

Classification head 35 may be or may include a machine learning model which may include a classification neural network that may be trained to process input 32 to determine a probability of a presence or absence of one or more morphological and/or flow abnormalities and/or a likelihood that one or more of the morphological and/or flow abnormalities is inconclusive. The neural network may extract features of frames of the image data and may generate an output indicative of a likelihood of a presence of a morphological abnormality. For example, classification head 35 may generate outputs indicative of overriding artery, septal defect at the cardiac crux, and/or abnormal relationship of the outflow tracts. In one example, the neural network of classification head 35 may be a vision transformer neural network. Vision transformers are a family of deep learning models which create linear embeddings from an input image. These embeddings may then be passed to a transformer encoder network which may create an embedding for the entire image. A classification head can then be used to convert this embedding into class predictions.

The vision transformer neural network may have three blocks: (i) a downsizing block used to resize the input image, (ii) a vision transformer neural network backbone or similar system that extracts features from each image, a (iii) a classification head that converts outputs into a probability of presence, absence or inconclusiveness for each classification radiographic finding. The downsizing block may take as input a preprocessed image and may resize it to a dimension using bilinear interpolation. The vision transformer neural network backbone may extract features for each frame of the video clip. The output of this block is an array with the number of input frames×the number of features. The classification head of the neural network may be a linear layer network followed by three independent softmax functions (e.g, 1 per radiographic finding). The linear network may take as input the features computed by the vision transformer neural network backbone, and output an array of the shape: number of input frames×3×3 (3 classes for each of the 3 classification findings, representing presence, absence and inconclusiveness for the finding). This array is then normalized into a probability array for each radiographic finding (representing the probability for presence, absence or inconclusiveness of a finding) using the 3 independent softmax functions.

Segmentation head 36 may be or may include a machine learning model which may include a segmentation neural network that may be trained to determine a counter, periphery and/or area interpretable or otherwise corresponding to certain anatomy in image data represented by input 32. The neural network may extract features from frames of the image data, may extract feature maps from the frames, and may generate an output indicative of contours of a plurality of anatomical features corresponding to the portion of the fetal anatomy. The segmentation neural network may be involved in the computation of enlarged cardiothoracic ratio and right ventricular to left ventricular size discrepancy, for example, and/or may detect the counter of certain anatomical features such as the counter of the left and right ventricles, the contour of the heart and the thorax. If there is no detection of an element by the algorithm or if a part of a detected element goes out of the image (e.g., if the image of the heart is cropped), this element may be marked as inconclusive for the respective frame. The segmentation neural network may independently perform predictions (e.g., absence, presence, or inconclusiveness) for each of the anatomical features. The detection head may be used for segmentation and may identify which of the anatomical features are detected with a confidence score. A threshold may be applied per anatomical feature to select only the most relevant predictions. Then, the segmentation head may generate binary masks for each detected object to accurately outline the shape of the anatomical structure. A contour may then be extracted from this binary mask. As a final process, each prediction having the highest confidence score for each anatomical feature may be selected. Anatomical features that are missing may be marked as inconclusive for that frame.

Key-point detection head 37 may be or may include a machine learning model which may include a neural network that may be trained to determine the positions of certain anatomy and/or points in the image data represented by input 32. The neural network may extract features from frames of the image data, may extract feature maps from the frames, and may generate an output indicative of coordinates of a plurality of anatomical features corresponding to the portion of the fetal anatomy. For example, a neural network may be trained to determine whether anatomy is present and/or is in the correct position (e.g., whether the heart and lungs are in the correct position). Additionally, or alternatively, locations of features of the patient's anatomy (e.g., heart and lungs) may be identified and distances between anatomy may be measured and compared to thresholds to determine whether the positions of certain anatomy is normal or abnormal. In one example, output of the trained neural network may be indicative of Heterotaxy syndrome.

The key-point detection neural network may generate outputs indicative of the presence of tricuspid valve to mitral valve annular size discrepancy, pulmonary valve to aortic valve annular size discrepancy, and/or cardiac axis deviation and/or may be indicative of the location the tricuspid valve, the mitral valve, the pulmonary valve, or the aortic valve as well as the long axis of the heart and/or the anteroposterior axis of the chest. If there is no detection of an element by key-point detection neural network or if a part of a detected element goes out of the image (e.g., if the image of the heart is cropped), this element is marked inconclusive for the respective image frame. The keypoint detection neural network may independently perform the predictions for each of the anatomical features.

The neural network utilized for key-point detection may be a Mask R-CNN model or similar model and/or may include a resizing block that resizes the input image. The resizing block may resize the image to have a minimum scale while preserving the aspect ratio (e.g., using bilinear interpolation). A ResNet-50-FPN backbone or similar system may then extract features from each image at various scales. A region proposal network and MultiScaleRoiAlign or similar system may then extract a set of fixed-size feature maps from these multi-scale feature maps of the backbone by detecting regions of interest that might contain anatomical features. The key-point detection head may then output the coordinates (e.g., cartesian coordinates) of the extremities for the anatomical features on the image.

As shown in FIG. 3B, model 33 may output neural network outputs 39 which may include output 38, output 40, and output 41. Output 38 may be output from classification head 35 and may be a probability of a presence or absence of a morphological and/or flow abnormality (e.g., overriding artery, septal defect at the cardiac crux, parallel great arteries, etc.). Output 40 may be output from segmentation head 36 and may identify data points corresponding to the image data forming contours of anatomy shown in the image data (e.g., contours of the left ventricle, right ventricle, heart, thorax, etc.). Output 41 may be output from key-point detection head 37 and may identify data points corresponding to the position in the image data of features of the anatomy represented in the image data (e.g., extremities of the tricuspid valve, extremities of the mitral valve, extremities of the pulmonary valve, extremities of the aortic valve, long axis of the heart, and/or anteroposterior axis of the chest).

Neural network outputs 39 may then be processed by post processing module 42. For example, output 38 may be processed by module 43 to determine whether morphological and/or flow abnormalities are absent or present or whether the absence or presence is inconclusive. For example, output 38 may be one or more vectors and may include a value indicative a probability of the presence, absence, and/or inconclusiveness of the presence or absence for each morphological and/or flow abnormality. Module 43 may process the vectors by comparing each to certain threshold values to determine whether each morphological and/or flow abnormality is absent, present or inconclusive. For example, for the morphological and/or flow abnormality "overriding artery," a vector may be output having the value 0.95 for present, 0.1 for absent, and, 0.1 for inconclusive. A threshold may be set at 0.9 for each of present, absent, and inconclusive, and the value 0.95 for present may then satisfy the threshold. As a result module 43 may determine that the abnormality "overriding artery" is present. It is understood that other thresholds and/or limits may be used to determine the presence, absence, and/or inconclusiveness of a morphological and/or flow abnormality.

Output 40 may be processed by module 44 which may determine measurements (e.g., area, length, volume, diameter, perimeter, and the like) for contours of anatomy shown in the image data, such as, for example, area of left ventricle, area of right ventricle, perimeter of the heart, and/or perimeter of the thorax. In one example, for particularly small or large features, the measurement may be only that the value is smaller or larger than a preset valve (e.g., smaller than 4 mm). These measurements may then be provided to and processed by module 47 which may determine ratios and/or comparisons of the measurements (e.g., area of the right ventricle divided by area of the left ventricle, perimeter of the heart divided by perimeter of the thorax, etc.). The ratios and/or comparisons may then be provided to and processed by module 50 which may determine the absence, presence, or inconclusiveness of certain abnormalities based on ratios and/or comparisons determined at module 47 by comparing such ratios and comparisons to thresholds and/or limits. In one example, module 50 may determine the presence, absence, or inconclusiveness of a right ventricle/left ventricle size discrepancy or the presence, absence, or inconclusiveness of an enlarged cardiothoracic ratio. For example, the valves determined by module 46 may be compared against threshold values to determine if such values exceed the threshold values. For example, the valves determined by module 47 may be compared against threshold values to determine if such values exceed the threshold values.

Output 41 may be processed by module 45, which may determine certain measurements (e.g., length, angle, area, etc.) based on features of the anatomy represented in the image data. For example, module 45 may determine values such as size (e.g., length, width, area) of the tricuspid valve, size of the mitral valve, size of the pulmonary valve, size of the aortic valve, and/or cardiac axis angle (e.g., angle between the long axis of the heart and the anteroposterior axis of the chest). The values determined by module 45 may be provided to module 46 which may demine ratios and/or comparisons based on the values. For example, ratios such as the size of the tricuspid valve divided by the size of the mitral valve, and/or the size of the pulmonary valve divided by the size of the aortic valve may be determined. The ratios and/or comparisons may then be provided to and processed by module 48 which may determine the absence, presence, or inconclusiveness of certain abnormalities based on ratios and/or comparisons determined at module 46 by comparing such ratios and comparisons to thresholds and/or limits. In one example, module 48 may determine the presence, absence, or inconclusiveness of a tricuspid valve versus mitral valve size discrepancy, a pulmonary valve/aortic valve size discrepancy, cardiac axis deviation. For example, the valves determined by module 46 may be compared against threshold values to determine if such values exceed the threshold values.

Representative frames of input 32 may be analyzed by analysis system 31. Alternatively, all image frames of input 32 may be analyzed by analysis system 31. In one example, measurements and other calculations performed by analysis system 31 may be performed on each image frame and the output may be combined to determine a single value. For example, a calculation of the area of the right and/or left ventricle may be calculated for each image frame, or each image frame clearly showing the anatomy, and the average, median, or mode of each calculation may be determined to determine a single value representative of the area of the right and/or left ventricle. The representative image frame showing the respective dimension may be selected and annotated to show the value on the image and/or arrows indicating the dimension. Alternatively, or additionally, metadata or other data may be associated with the image and include such information. Such a value may be used to determine if an abnormality is present or absent. By combining the calculations or measurements of multiple frames, a more accurate calculation or measurement may be determined than a value from single image frame and thus a more accurate determination of a presence or absence of an abnormality may be made.

In determining whether certain calculations, measurements, and/or other positional information is indicative of an abnormality, a gestational age may be determined. For example, the gestational age may be input by a user and certain thresholds and/or models (e.g., neural networks) may be adjusted and/or selected based on and corresponding to the gestational age. In one example, the length of the femur may be measured. In another example, a neural network may be trained to estimate a gestational age based on the image data and such estimated age may then be used to adjust and/or select certain thresholds and/or models for determining whether abnormalities are present. For example, a neural network may be trained to automatically determine the length of femur, which then may be used to adjust and/or select certain thresholds and/or models for determining whether abnormalities are present.

Thresholds and limits indicative of a presence of an anomaly may be based on measurements informed by the general population and/or may be adjusted based on gestational age. Scores (e.g., z-scores) may be determined for differences between the patient's measurement and the measurement corresponding to the general population. Additionally, thresholds and other analysis may be adjusted and/or modified according to known correlations based on information from other individuals and/or the general population. For example, certain measurements or presence of a type of abnormality may increase the likelihood of a certain other abnormality. Accordingly, if a certain measurement is above or below a threshold value and/or one type of abnormality is determined to be present, a threshold and/or limit for determining the presence of another abnormality may be adjusted (e.g., the threshold for detecting the other type of anomaly may be lowered). This is referred to as adjusting the sensitivity for the abnormality. For example, a patient determined to have asymmetric ventricles may be more likely to have an overriding artery and thus a threshold value for determining that an overring artery is present may be lowered to increase sensitivity to the overriding artery being present.

In another example, if the measurement of the area of the heart (e.g., meaning its dimension or its z-score at a given gestational age and optionally normalized by the patient's thorax) is above a certain threshold valve, then threshold values for detecting a presence of septal defect at the cardiac crux, overriding artery, and abnormal relationship of the outflow tracts may be adjusted to be more sensitive (e.g., by lowering such threshold value). In yet another example, if (i) the annulus size of the pulmonary valve (e.g., meaning its dimensions or its z-score at a given gestational age and optionally normalized by the annulus size of the aortic valve) is too large or too small, (ii) the annulus size of the tricuspid valve (e.g., meaning its dimensions or its z-score at a given gestational age and optionally divided by the annulus size of the mitral valve) is too small or too large, or (iii) the area of the right ventricle (meaning its dimensions or its z-score at a given gestational age and optionally normalized by the area of the left ventricle) is too small or too large, then thresholds indicating the presence of overring artery and abnormal relationship of the outflow tracts may be made more sensitive (e.g., lowered). The foregoing examples are non-limiting and it will be understood by one of ordinary skill in the art that adjusting thresholds indicative of a presence of an abnormality may generally be used for any correlated abnormalities, conditions, measurements or the like.

The adjustments made to the thresholds and limits to increase sensitivity may be a single adjustment, tiered adjustments, or a sliding scale of adjustments. For example, a single adjustment means that if a first measurement satisfies a certain threshold a second threshold for an abnormality is made more sensitive by changing the threshold one time to a different value. Tiered adjustments means that a first measurement (e.g., of the area of the heart) satisfying a first threshold will result in adjustment of the second threshold to be more sensitive and a second measurement (e.g., of the area of the heart) will result in an adjustment of the second threshold to be even more sensitive and so on. A sliding scale adjustment means that a threshold value indicative of a certain anomaly will be continuously adjusted to different values to be more sensitive depending on the value of a measurement (e.g., the greater the area of the heart, the lower the detection threshold for determining a presence of an abnormality). In one example, a default threshold for identifying a tricuspid valve to mitral valve annular size discrepancy may be (1.6, 0.85) but if the area of the heart is determined to be too high (e.g., above a certain threshold value), then the threshold for identifying the tricuspid valve to mitral valve annular size discrepancy may be adjusted and replaced with (1.55, 0.8).

Figure 4A:
Figure 4B:
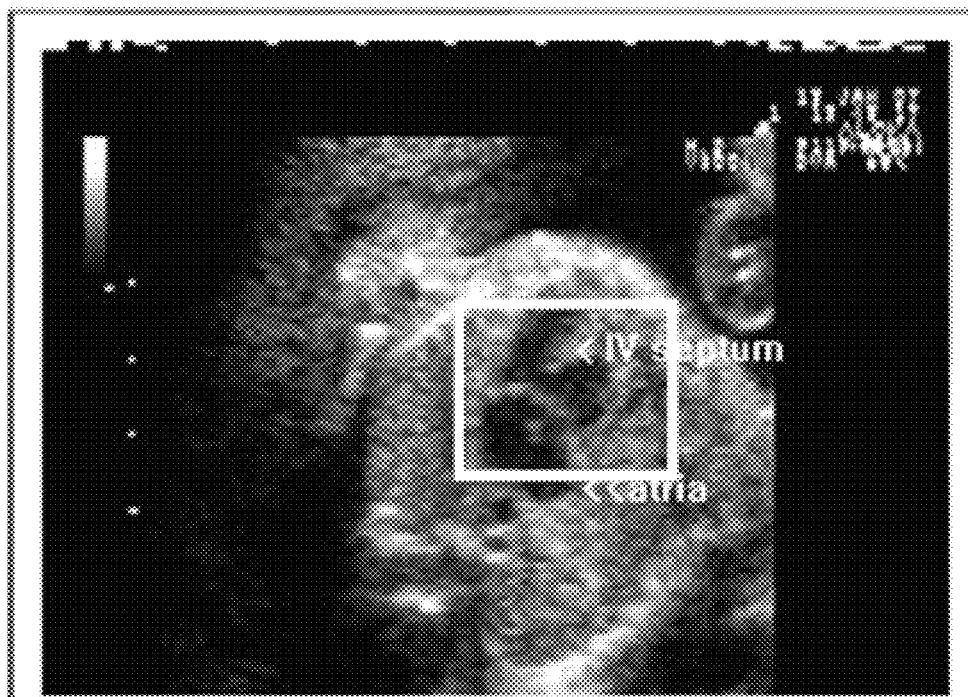

Referring now to FIGS. 4A and 4B, examples of screen displays that may be presented at display computer 20 corresponding to clicking on the text labels identified in FIG. 2 are described. As noted above, if a standard view is identified by the interpretative component as being present in the motion video clips transmitted to server computer 30, a checkmark will appear in column 52 in FIG. 2. As previously described, clicking on the checkbox will cause the raw image selected by the interpretative component to be displayed on display computer 20. Clicking on the "None" label in column 53 will cause the selected image frame, annotated with the overlay generated by the interpretative component, to be displayed on display computer 20. FIG. 4A is an example of an image frame corresponding to a 4C standard view, without abnormalities and with the foramen ovale identified. FIG. 4B is an example of a selected image frame corresponding to a standard 4C view, in which a large atrioventricular defect is detected. In FIG. 4B, the defect is surrounded with a white bounding box; other cardiac structures are identified by textual and graphical labels.

Figure 5:
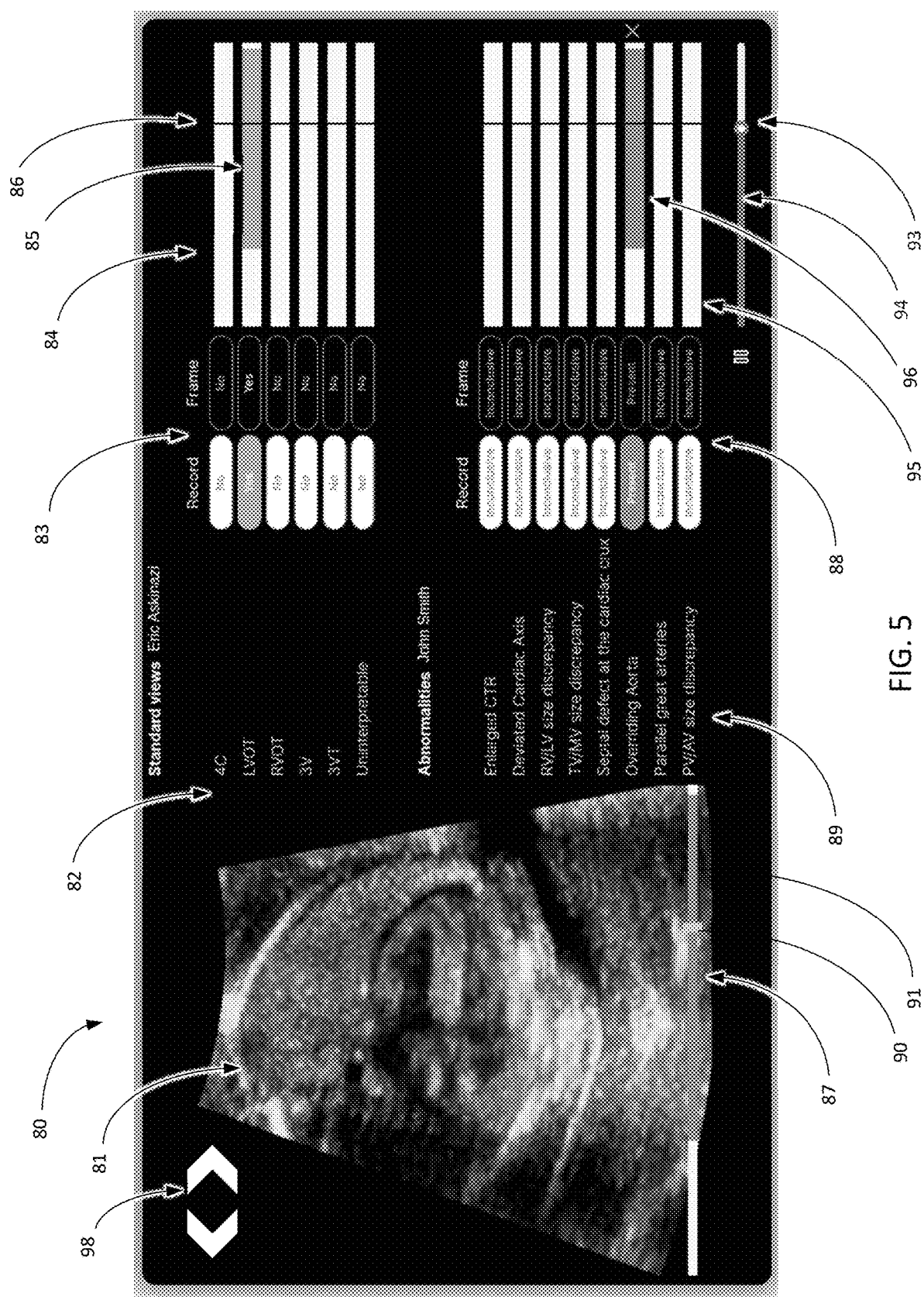
FIG. 5 is an exemplary graphic user interface including a representation of the image of the patient and a list of standard views and abnormalities.

Referring now to FIG. 5, an exemplary graphic user interface is depicted including at least a portion of the image and/or video captured by an imaging system (e.g., ultrasound imaging system), a list of standard views, and a list of abnormalities. Graphic user interface 80 may be a digital display and may be presented on a device (e.g., computing device, laptop, desktop, tablet, smartphone, display, etc.) of a healthcare provider. Graphic user interface 80 may present information about whether the image corresponds to a type of standard view and/or whether a certain abnormality or condition is present in the image from the imaging system.

As shown in FIG. 5, image 81 may be an image frame from a video clip generated by an imaging system (e.g., an ultrasound video frame and/or clip). Time bar 87 may include cursor 90 that may move along the time bar to indicate a time point along the video clip corresponding to the image presented in image 81. Time bar 87 may further include indicator 91 which may visually indicate (e.g., via color or marker) the presence and location of an abnormality in the video clip. Cursor 90 may be moved along time bar 87 to a an image frame or other time point in the time bar corresponding to an abnormality and/or standard view. Moving cursor 90 may then cause image 81 to change to the image frame at the respective time point. In one example, image 81 may be annotated with color, bounding boxes, text, or other visual indicators to identify the location of the abnormality in image 81.

Standard view list 82 may include a list of standard imaging views (e.g., 4C, LVOT, RVOT, 3V, 3VT, etc.). Any other image view other than those listed in FIG. 5 may alternatively or additional be included. For each standard view, image 81 includes record and frame indicator 83, which identifies whether or not a record is present for each view and whether or not a representative frame is identified for each view. Time bars 84 are also included for each view and are commensurate in length with the length of time of a given video clip. For each time bar, a visual indicator (e.g., visual indicator 85) is included to show where in the video clip the given standard view appears. If no visual indicator is provided for a given time bar, then the respective standard view does not appear in the video clip. Cursor bar 86 is also included on time bars to indicate the location on time bars 84 that corresponds to the image frame presented at image 81.

Abnormality list 89 may include a list of abnormalities and/or conditions corresponding to image 81. For example, abnormality list 89 may include enlarged CTR, cardiac axis deviation, RV/LV size discrepancy, TM/MV size discrepancy, septal defect at the cardiac crux, overriding artery, parallel great arteries, PV/AV size discrepancy, abnormal outflow tracts relationship, and/or any other abnormality and/or condition. For each abnormality and/or condition, graphic user interface 80 includes record and frame indicator 88, which identifies whether or not a record is present for each view and whether or not a representative frame is identified for each view. For purposes of identifying whether a record is present or absent, if at least one frame of the record is identified as present, any other frames identified as absent will be disregarded or relabeled as inconclusive.

Time bars 95 are also included for each view and are commensurate in length with the length of time of a given video clip. For each time bar of time bar 95, visual indicator 96 is included to show where in the video clip the given view appears. If no visual indicator is provided for a given time bar, then the given abnormality or condition corresponding to the time bar does not appear in the respective video clip. Cursor bar 86 may also be included on time bars to indicate the location on time bars 95 that corresponds to the image frame presented at image 80.

Time bar 94 may also be included below time bars 84 and time bars 95 and may indicate the location of cursor bar 86 along the length of the respective video clip via cursor 93. Moving cursor 90, cursor bar 86, and/or cursor 93 may cause the other cursors and/or cursor bars to respectively move. Time bar 94 may include a play and/or pause button. When the play button is engaged, the video clip may play, showing the various image frames of the video clip in image 81. As the video clip progresses in image 81, cursor bar 86 and cursors 90 and 93 may progress along their respective time bars. When the pause button is engaged, the video clip may be paused. Graphic user interface 80 may optionally include buttons 98 to move to the next or previous video clip.

Figure 6:
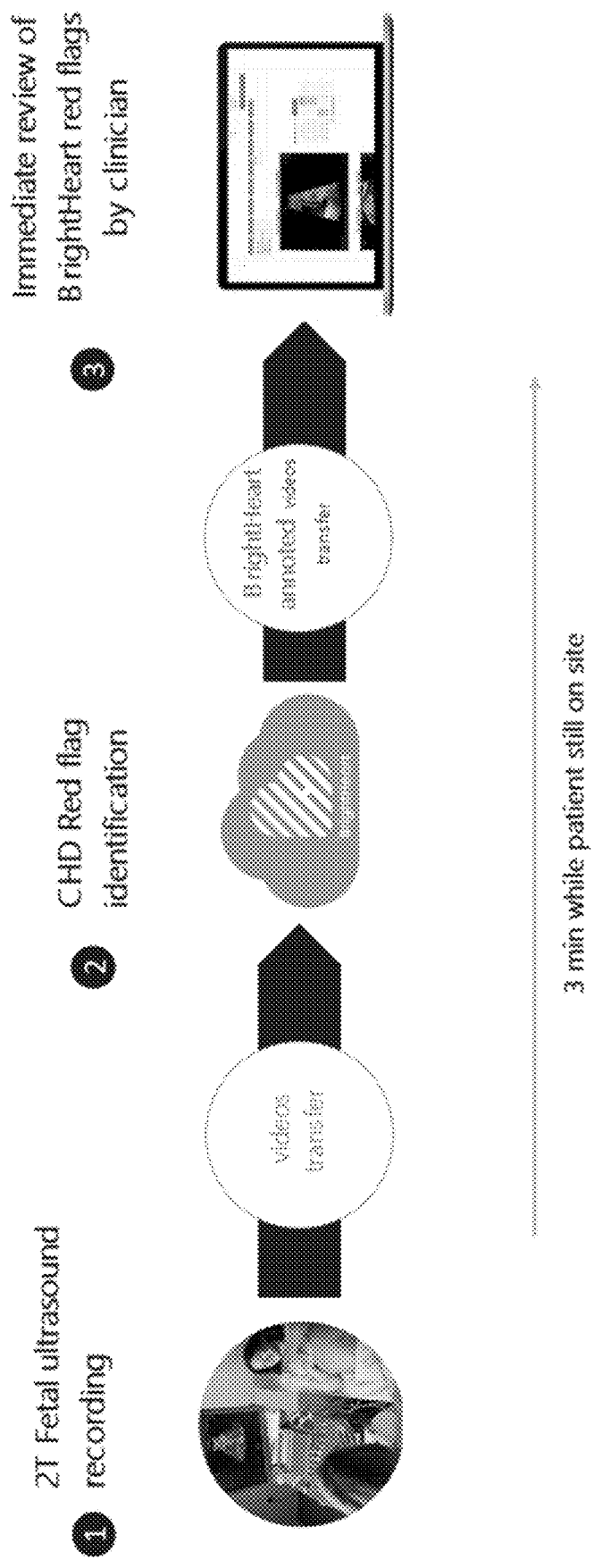
FIG. 6 is an exemplary data flow for obtaining medical images, identifying red flags, annotating the images, and providing the flagged and annotated images in a graphic representation.

Referring now to FIG. 6, an exemplary process flow for obtaining medical images, identifying red flags, annotating the images, and providing the flagged and annotated images in a graphic representation is depicted. As shown in FIG. 6, fetal images (e.g., 2T fetal ultrasound images, videos, and/or recordings) are generated and transferred to a platform, which may be a cloud-based platform on a server which may be a remote server or a local server. The platform may process the images using techniques described herein to identify red flags (e.g., the presence of anomalies, abnormalities, and/or conditions in the images). The images may be annotated to indicate the presence of the anomalies, abnormalities, and/or conditions. Alternatively, or additionally, metadata or other data may be associated with the image and include such information. The annotated images may be presented to a health care provider (e.g., clinician) on a healthcare provider device for immediate or near immediate (e.g., 1 min, 2 min, 3 min, 4 min, 5 min, 10 min, etc.) review by the healthcare provider. The review by the healthcare provider may occur while the patient is onsite. The device that generates the images and/or the healthcare provider device may be in wireless communication (e.g., via the internet) with the platform. The healthcare provider device and the imaging device may be the same or different devices.

Figure 7:
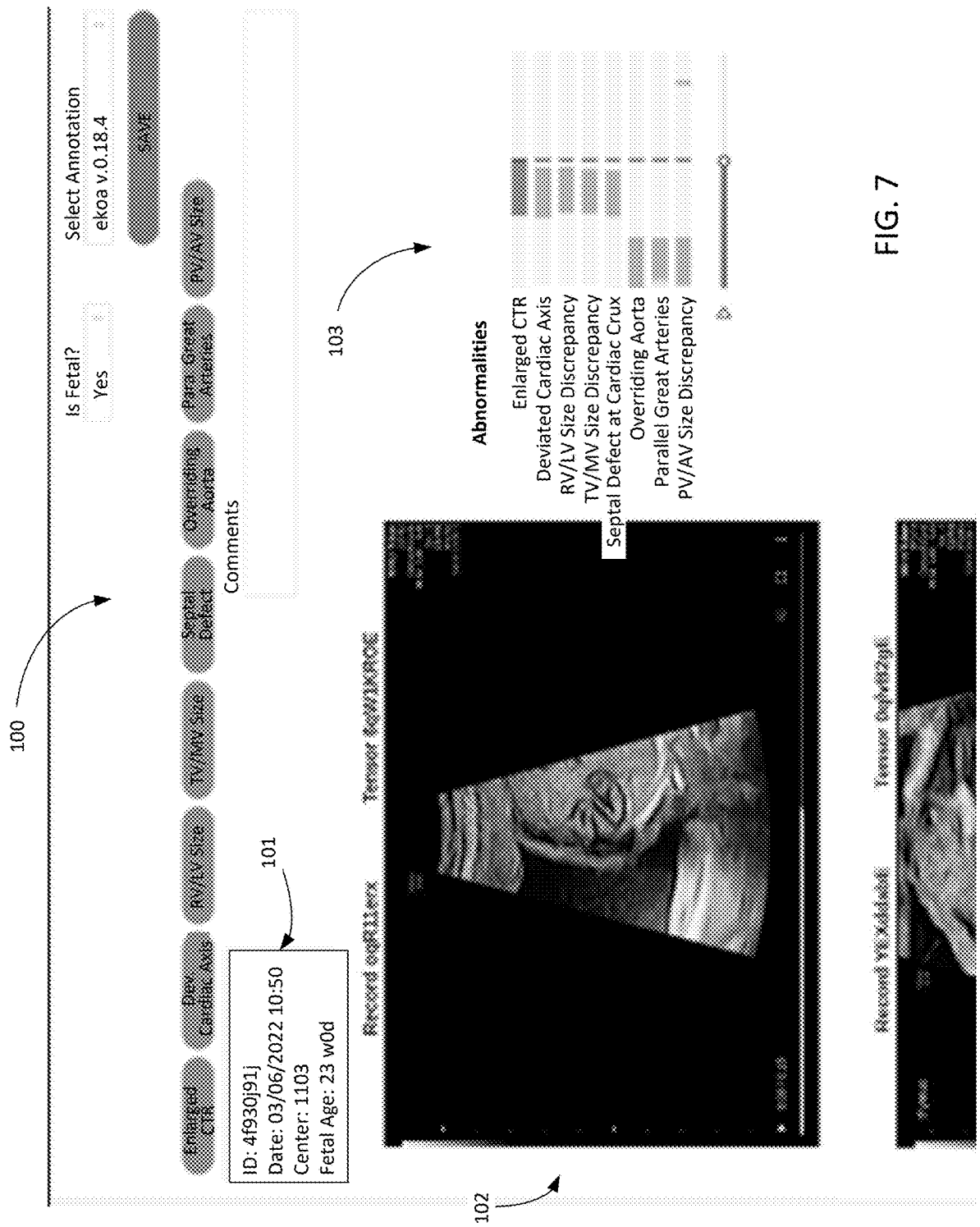
FIG. 7 is an exemplary graphic user interface including a representation of the images of the patient, patient information, and a list of abnormalities.

Referring now to FIG. 7, an exemplary graphic user interface including a representation of images of the patient, patient information, and a list of abnormalities is depicted. Graphic user interface 100 may include patient information 101 include a patient ID, the healthcare provider center, the date, the time, and any other relevant information. Graphic user interface 100 may further include images 102 which may include a play and/or pause button for playing a video of the images (e.g., ultrasound video). A user may scroll to the next video or image by moving the graphic user interface up and down.

Graphic user interface 100 may further include abnormality analysis 103 for each image 102, which may include a list of abnormalities and for each abnormality a time bar may be provided on which a visual indicator may indicate whether that respective abnormality is present in the video. The visual indicator may be a color bar which may extend the portion of the time bar for which the abnormality is present. The time bars may include a cursor for indicating the location along the time bar corresponding to the image frame present on image 102. Abnormality analysis may further include a time bar with a cursor and a pause and play button. Moving the cursor, and/or engaging pause or play may cause image 102 to move to a certain time point, to pause, or to play.

Figure 8A:
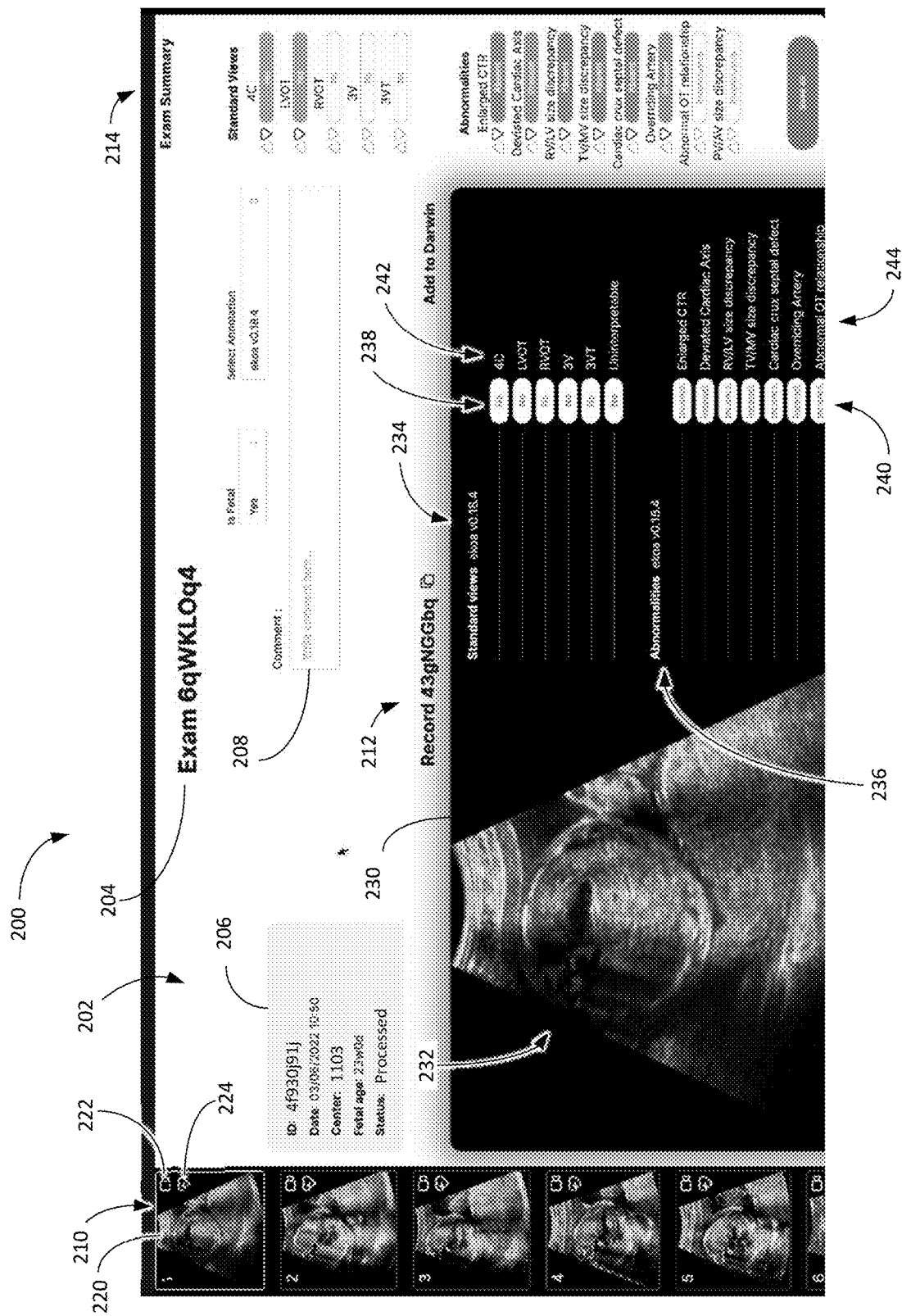
FIGS. 8A-8C are exemplary user interfaces for displaying image data generated by an ultrasound system as well as standard view and abnormality indicators
Figure 8B:
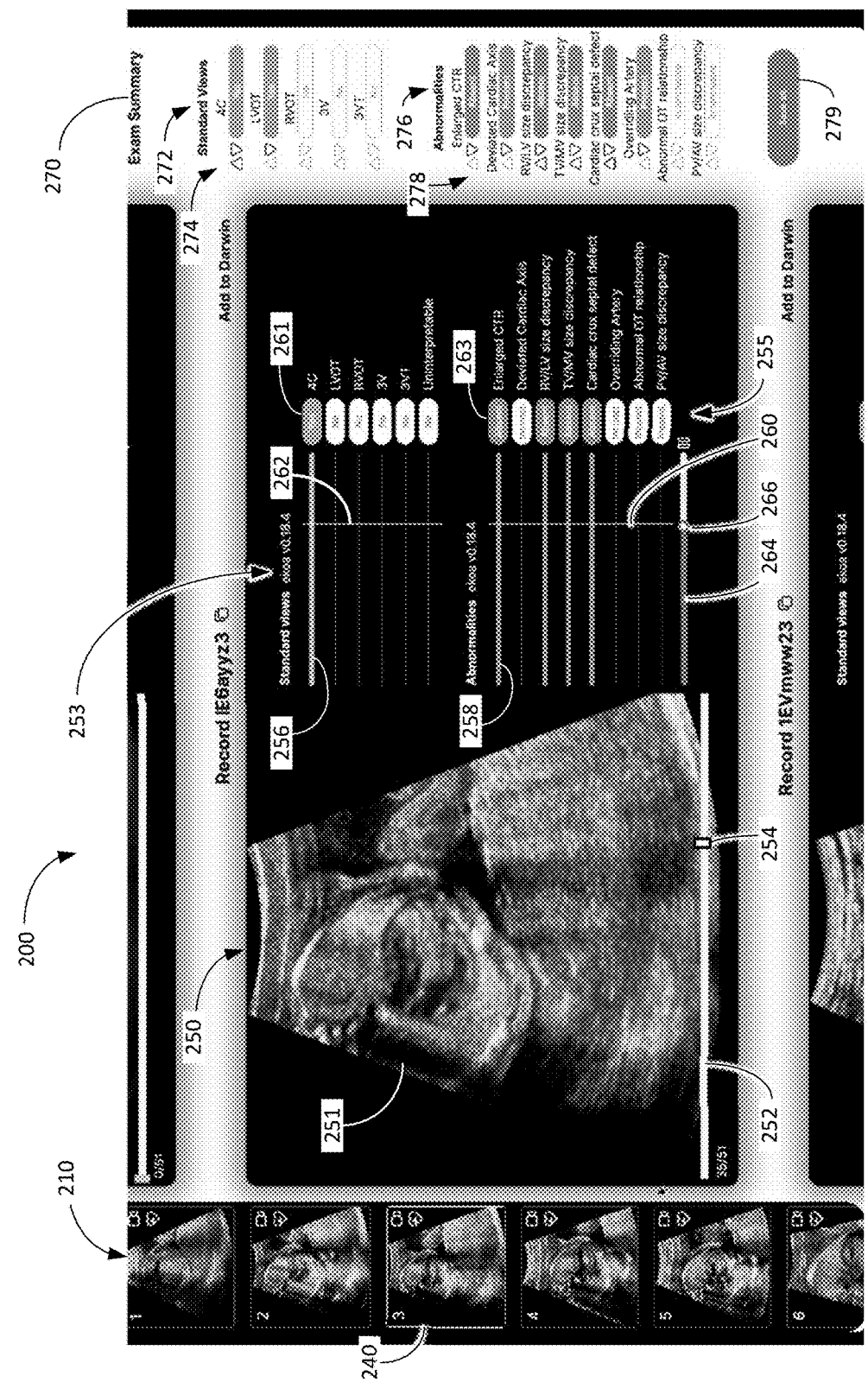
Figure 8C:
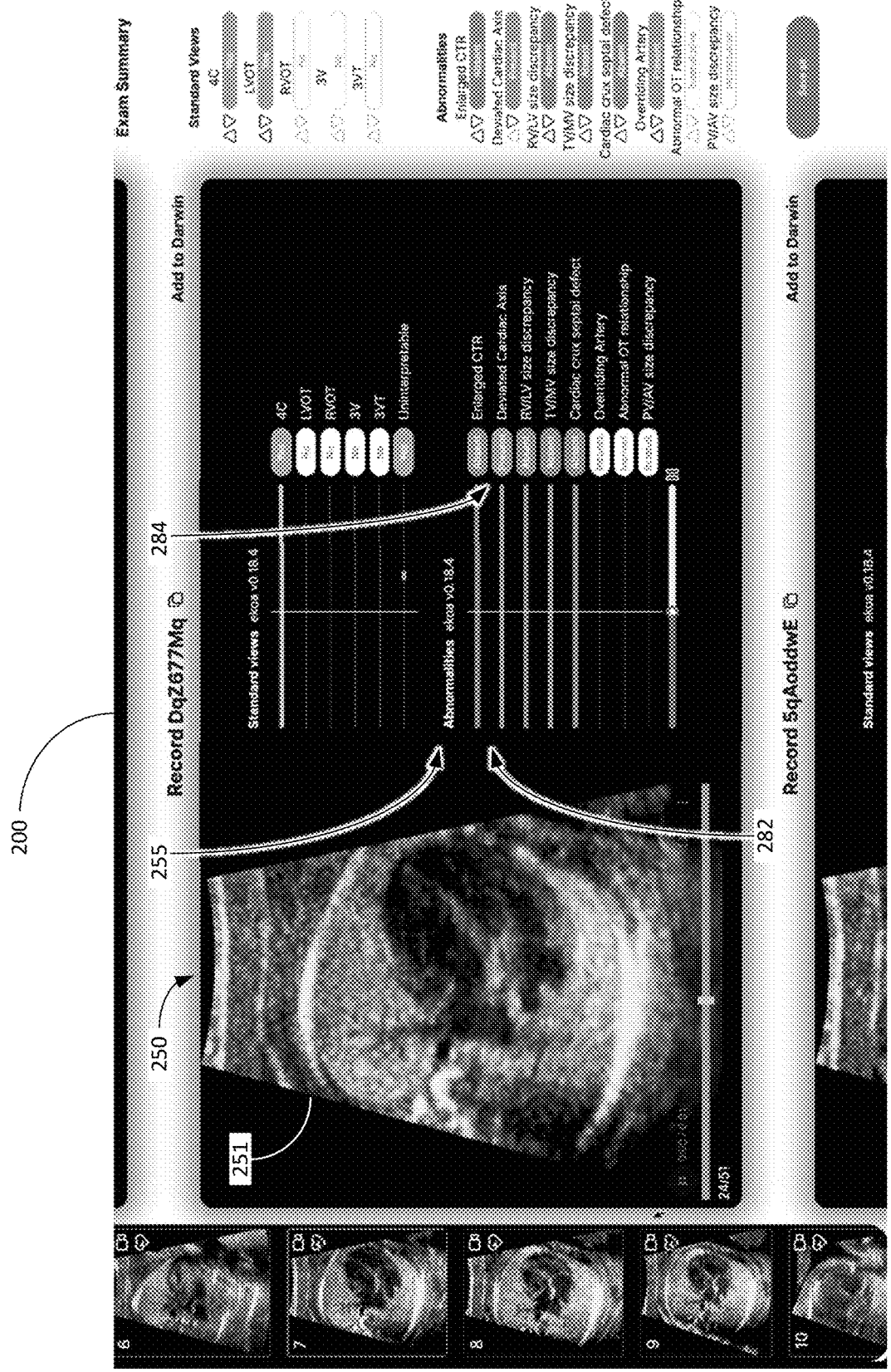

Referring now to FIGS. 8A-8C, exemplary user interfaces for displaying image data generated by an ultrasound system as well as standard view and abnormality indicators are illustrated. For example, user interface 200 of FIG. 8A may be generated by an ultrasound system (e.g., ultrasound system 10 of FIG. 1B). User interface 200 may be presented on display computer 20 of ultrasound system 10 and/or display 22 of healthcare provider device 25.

User interface 200 may include user section 202 which may include exam title, which may be an identifier for an ultrasound examination, user information 206, which may include a user identifier (ID), a date, center data, age of the fetus, age of the mother, a status (e.g., processed), and the like. User section 202 may include comment portion 208 for a technician or other healthcare provider to make notes about an examination and/or about a set of image data (e.g., video clip).

User interface 200 may further include thumbnail viewer 210, detailed viewer 230, and exam summary 214. Thumbnail viewer 210 may be a collection of thumbnail images, each corresponding to a video clip and/or image frame generated by ultrasound device 10. For example, during an ultrasound examination, image data such as image clips and/or image frames may be generated. In one example, a thumbnail image for each video clip generated for a given examination may be included in thumbnail viewer 210. Thumbnail viewer 210 may further include video indicator 222 which may visually indicate whether or not the image data includes a video clip, and/or indicator 224, which may visually indicate whether or not the fetal heart is interpretable in at least one frame of the corresponding set of image data. For example, if the set of image data is corrupt or if the fetal heart is not present in the set of image data, indicator 224 may not be included in thumbnail viewer 210 or otherwise indicator 224 may visually indicate that the fetal heart is not interpretable.

Each set of image data (e.g., video clip and/or one or more image frame) generated during an examination may be viewed in detailed viewer 230 (e.g., by clicking on a thumbnail image (e.g., thumbnail image 220) of thumbnail viewer 210. For example, detailed viewer 230 may correspond to thumbnail image 220. A user may click on a different thumbnail image in thumbnail viewer 210 to update detailed viewer 230 to present the set of image data corresponding to thumbnail image 220.

Detailed viewer 230 may include image data viewer 232, standard view indicator 234, and morphological anomaly indicator 236. Image data viewer 232 may present a video clip and/or still frame of the image data (e.g., the set of image data corresponding to thumbnail image 220). Standard view indicator 238 may include list of standard views 242 and color indicators 238 indicating whether or not each standard view in list of standard views 242 is present in the image data or if the presence of such standard view is inconclusive. For example, a color indicator may indicate whether or not a certain standard view is present in the image data (e.g., using different colors for present and absent).

Morphological abnormality indicator 236 may include list of morphological abnormalities 244 and color indicators 240 indicating whether or not each morphological abnormality in the list of morphological abnormalities is present in the image data. For example, color indicator 240 may indicate whether or not a certain morphological abnormality is present in the image data or alternatively if the presence of the morphological abnormality is inconclusive. The color indicator for standard view indicator 234 may be different than the color indicator for morphological abnormality indicator 236 (e.g., each using different and unique colors for present and absent). Also, a different and unique color may be used for inconclusive.

Referring now to FIG. 8B, user interface 200 may be adjusted by the user to present detailed viewer 250, thumbnail viewer 210, and exam summary 270. A user may select thumbnail image 240 of thumbnail viewer 210 and/or otherwise navigate user interface 200 to view detailed viewer 250, which may correspond to thumbnail image 240. Detailed viewer 250 may be the same as or similar to detailed viewer 230 of FIG. 8A. Detailed viewer 250 may include image data viewer 251 which may include a still frame or video clip of image data (e.g., the set of image data corresponding to thumbnail image 240). Time bar 252 may be included in detailed viewer 250 and as well as cursor 254 which may indicate a time point along the time bar corresponding to the image frame presented in image data viewer 251.

Detailed viewer 250 may further include standard view indicator 253 and morphological abnormality indicator 255, which may be the same as or similar to standard view indicator 234 and morphological abnormality indicator 236 of FIG. 8A. As shown in FIG. 8B, the standard view "4C" may be present in standard view indicator 253 and with color indicator 261 indicating "yes" for present, which is presented in blue. Several morphological abnormalities are indicated as being absent in morphological abnormality viewer 255 such as enlarged CTR, RV/LV size discrepancy, TV/MV size discrepancy, and cardiac crux septal defect. The other abnormalities in morphological abnormality viewer 255 are indicated as being inconclusive. Color indicator 263 may show green to indicate a presence of each of the abnormalities in the image data presented in image data viewer 251 and white to indicate inconclusive.

Standard view indicator may also include a time bar for each standard view in the list of standard views. For example, time bar 256 may correspond to the standard view "4C." Similarly, morphological abnormality indicator 255 may include a time bar for each abnormality in morphological abnormality viewer 255. For example, time bar 258 may correspond to enlarged CTR. Each time bar may present a color along some or all of the time bar when the corresponding standard view or abnormality is determined to be present or absent in the image data. For example, time bar 256 may be blue to indicate the presence of standard view "4C" and time bar 258 may be green to indicate an absence of enlarged CTR.

Each time bar for standard view indicator 253 and morphological abnormality viewer 255 may include a visual indicator that moves together with cursor 254. For example, time bar 256 may include visual indicator 262 and time bar 258 may include visual indicator 260. Additionally, below each time bar for standard view indicator 253 and morphological abnormality viewer 255, time bar 264 may be included which may be aligned with each time bar (e.g., time bar 256 and time bar 258) and may include a cursor that aligns with visual indicators 262 and 260, which may be used by user to move cursor 254 to different time points along time bar 252.

User interface 200 may further include exam summary 270 which may include standard view summary 272 and abnormality summary 276 which may summarize standard views and morphological abnormalities determined to be present, absent, or inconclusive in the sets of image data uploaded from the ultrasound system. Standard view summary 272 may include a list of standard views as well as a color indicators to indicate whether or not each standard view is present, absent, or inconclusive. Standard view summary 272 may include advance buttons 274 for each standard view which may be used by a user to advance user interface 200 to a detailed viewer including image data with the standard view present and may automatically adjust the image data viewer such that an image frame with the standard view present is in view. For example, each time advance button 274 is engaged, the next image frame determined to correspond to the respective standard view will be displayed in the detailed viewer permitting the user to efficiently view image frames and/or sets of image data corresponding to the standard views. Exam summary 270 may permit a user to efficiently determine whether a view and/or abnormality is absent, present, or inconclusive (e.g. whether or not at an abnormality is inconclusive).

Exam summary 276 may further include abnormality summary 272. Abnormality summary 276 may include a list of abnormalities as well as color indicators to indicate whether or not each abnormality is present. Abnormality summary 276 may include advance buttons 278 for each abnormality which may be used by a user to advance user interface 200 to a detailed viewer including image data with the abnormality present and may automatically adjust the image data viewer such that an image frame with the abnormality present is in view. For example, each time advance button 278 is engaged, the next image frame determined to correspond to the respective abnormality will be displayed in the detailed viewer permitting the user to efficiently view image frames and/or sets of image data corresponding to the abnormalities. User interface 200 may further include a save button 279 to save any image data, images, determinations, and/or data from user interface 200, settings, notes, comments, or the like.

Referring now to FIG. 8C, detailed viewer 250 of user interface 200 may be updated to indicate that an abnormality has been determined to be present in the image data. For example, morphological abnormality indicator 255 may be updated to change color indicator 284, corresponding to deviated cardiac axis, to red to indicate that the image data presented in image data viewer 251 defines a "deviated cardiac axis." Time bar 282 may be changed to the same color as color indicator 255 (e.g., red) to indicate the presence of the morphological abnormality. Time bar 282 may alternatively be changed to the same color as the "absence" indicator (e.g., green) to indicate one or more frames along the time bar corresponding to an absence of the abnormality. Alternatively, only portions of time bar 282 corresponding time points in the image data associated with image frames showing the abnormality will be colored.

Figure 9:
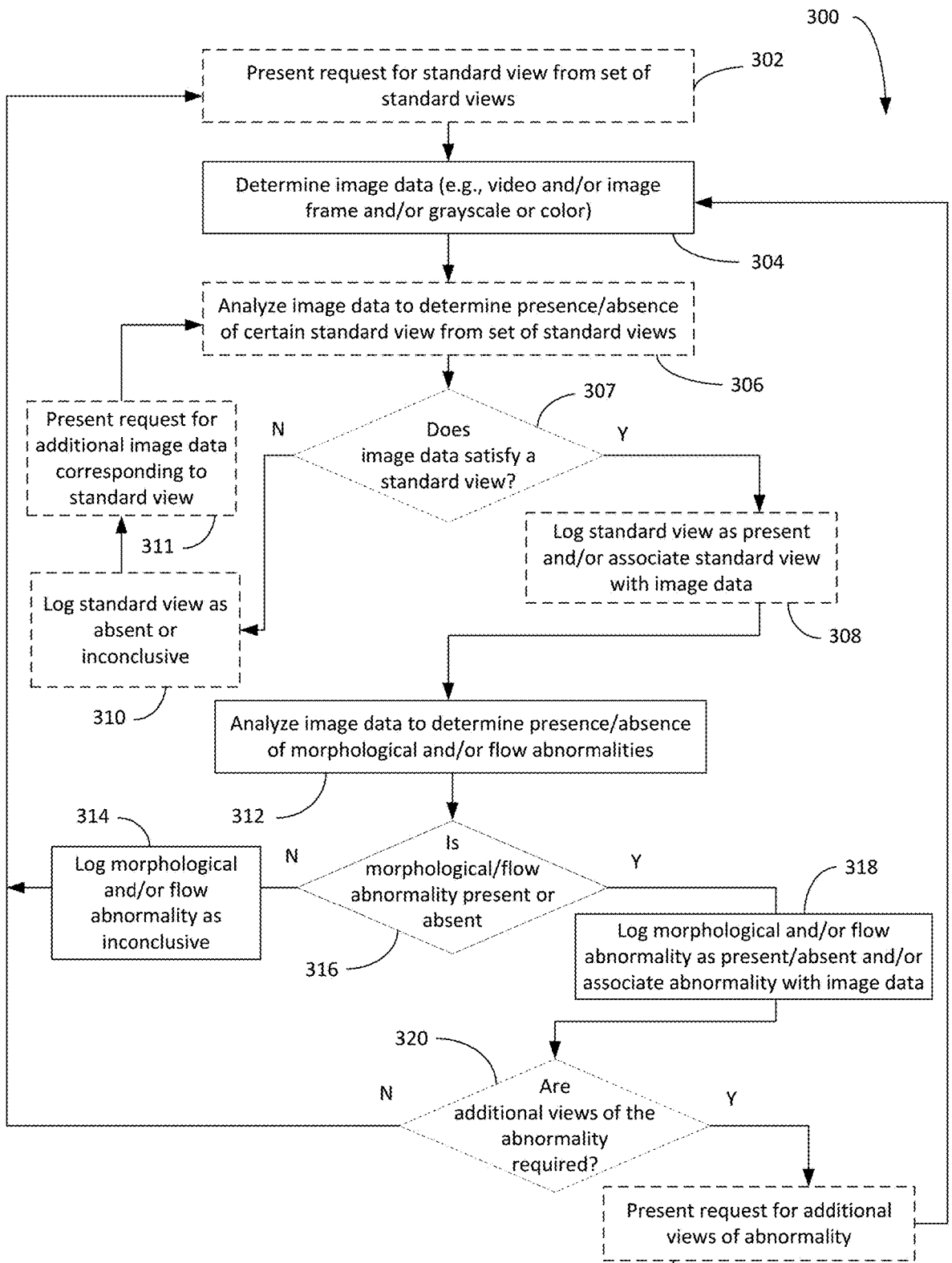
FIG. 9 is an exemplary flowchart for dynamically requesting additional image views and logging the presence and absence of standard views and morphological abnormalities.

Referring now to FIG. 9, process flow 300 is illustrated for dynamically requesting additional image data based on the presence or absence of standard views and morphological abnormalities in the image data. Some or all of the blocks of the process flows in this disclosure may be performed in a distributed manner across any number of devices. Some or all of the operations of the process flow may be optional and may be performed in a different order. Image data may be any medical imaging data, such as image data from an ultrasound system, for example. The image data from an ultrasound system may be greyscale ultrasound images and/or Doppler ultrasound images (e.g., color Doppler ultrasound, Power Doppler ultrasound, etc.).

At optional block 302, computer-executable instructions stored on a memory of a device, such as a server and/or computer of an ultrasound system (e.g., display computer 20 of FIG. 1B), may be executed to present a request for image data (e.g., image frames, video clips, etc.) having a certain standard view (e.g., 4C) from a predetermined set of standard views. For example, a list of standard views that should be collected in an ultrasound examination may be predetermined. At block 304, computer-executable instructions stored on a memory of a device, such as a server and/or computer of an ultrasound system, may be executed to determine image data (e.g., image frames, video clips (e.g., that less than 1 second, between 1 second and one minute, or between 1 minute and one or more hours), etc.). For example, the ultrasound system may present a prompt for certain image data and a user may generate the image data using the ultrasound system, which may include an ultrasound probe.

At optional block 306, computer-executable instructions stored on a memory of a device, such as a server and/or computer of an ultrasound system, may be executed to analyze the image data to determine a presence or absence of a certain standard view from the set of standard views. For example, the image data may be processed using the approach described above with respect to FIG. 3A. Alternatively, the image data may be processed by one or more machine learning models trained to detect standard views from image data. For example, a machine learning model may be trained using images and/or video clips known to represent a standard view and the trained model may identify a type of standard view or otherwise generate an output indicating that a standard view is not present in the image and/or video clip. At optional decision 307, computer-executable instructions stored on a memory of a device, such as a server and/or computer of an ultrasound system, may be executed to determine whether the image data satisfies a standard view (e.g., whether the standard view is present in the image data).

In one example, at optional decision 307, image data may be determined to satisfy a standard view only if the view is present for a certain period of time (e.g., 0.5 seconds, 1 second, 3 seconds, 5 seconds, etc.). The period of time may be in the aggregate, meaning an aggregation of all frames and/or clips showing the view in question. Alternatively, the period of time may be continuous time, meaning the standard view must be deemed present continuously for the set period of time (e.g., 1 second).

Additionally, the image data may optionally be pre-processed by one or more machine learning models trained to detect anatomy in the video clip and determine whether heart and/or cardiovascular anatomy is present. For example, the one or more machine learning algorithms may be trained to determine if the video clips shows a heart, thorax and/or cardiovascular system. If it is determined that the video clips do not show a heart or other cardiovascular anatomy, or the thorax, such video clip may be discarded or otherwise ignored.

If a certain standard view is determined not to be present or if it is inconclusive whether the standard view is present in the image data, at optional block 310, computer-executable instructions stored on a memory of a device, such as a server and/or computer of an ultrasound system, may be executed to log or otherwise note that a certain standard view is absent in the image data or if it is not clear whether the certain standard view is present or absent, then log or otherwise note that it is inconclusive whether the certain standard view is present. Further, one or more time points (e.g., time stamps) in the image data may be associated with the certain standard view being absent or inconclusive in the image data. At optional block 311, computer-executable instructions stored on a memory of a device, such as a server and/or computer of an ultrasound system, may be executed to present a request for additional image data corresponding to the certain standard view.

Alternatively, if a certain standard view is determined to be present in the image data, at optional block 308, computer-executable instructions stored on a memory of a device, such as a server and/or computer of an ultrasound system, may be executed to log or otherwise note that the certain standard view is present in the image data and may associate one or more time points (e.g., time stamps) in the image data with the certain standard view. A representative still frame showing the standard view may be selected from the video clip. For example, a still frame clearly showing the standard view may be selected from a one second video clip showing the standard view. Optionally, the standard view may be labeled with text. For example, textual indicators may be applied to each representative image for each standard view (e.g., 4C, LVOT, 3V and 3VT).

Upon determining that a certain standard view is present and/or logging or otherwise noting that the certain standard view is present, if image data corresponding to that view is determined to include an abnormality, such abnormality may be identified and/or displayed as present. Prior to determining that a certain view is present, all abnormalities for such view will be identified and/or displayed as inconclusive. In another example, an indication of whether each abnormality and/or finding is present, absent, or inconclusive may be displayed or accessible once certain standard views are determined to be present. For example, once 4C, LVOT, and RVOT are determined to be present, an indication of whether each finding and/or abnormality is present, absent, or inconclusive may be displayed and/or otherwise accessible. While 4C, LVOT, and RVOT are used as examples, any other standard views may be selected and any number and/or combination of standard views may be selected. In yet another example, each finding and/or abnormality may correspond to a threshold value for determining whether such finding and/or abnormality is present and further may correspond to a heightened threshold value (e.g., larger than the threshold value used to determine whether such finding and/or abnormality is present), which if satisfied, may result in the presence of the finding and/or abnormality being immediately displayed and/or accessible not withstanding whether or not any standard views have been determined to be present.

At block 312, computer-executable instructions stored on a memory of a device, such as a server and/or computer of an ultrasound system, may be executed to analyze the image data to determine a presence or absence of a certain morphological and/or flow abnormalities from the set of morphological and/or flow abnormalities. For example, the image data may be processed using the approach described above with respect to FIG. 3A. Optionally, block 312 may be initiated after block 310 as well as after block 308.

In yet another example, decision 307 and blocks 306, 308, 310, and 311 may all be optional, and block 312 may be initiated immediately after block 306. The image data analyzed at block 312 may be an entire video clip. For example, the video clip may be made up of multiple image frames and each frame of the video clip may be analyzed at block 312 to determine the presence or absence of morphological and/or flow abnormalities.

At decision 316, computer-executable instructions stored on a memory of a device, such as a server and/or computer of an ultrasound system, may be executed to determine whether or not the morphological and/or flow abnormality is present or absent. If it is not clear whether the morphological and/or flow abnormality is present or absent, at block 314, computer-executable instructions stored on a memory of a device, such as a server and/or computer of an ultrasound system, may be executed to log or otherwise mark the morphological and/or abnormality as inconclusive as it is not clear whether the abnormality is present or absent at one or more time points (e.g., time stamps) associated with the image data. Alternatively, if it determined that the morphological and/or flow abnormality is present or absent, at block 318, computer-executable instructions stored on a memory of a device, such as a server and/or computer of an ultrasound system, may be executed to log or otherwise mark the morphological and/or flow abnormality as present or absent, as appropriate, and/or associate the presence or absence of such abnormality with one or more time points in the image data. If the morphological or flow abnormality is determined to be present, a representative still frame showing the morphological or flow abnormality may be selected from the video clip. For example, a still frame clearly showing the morphological or flow abnormality may be selected from a one second video clip. Optionally, the morphological or flow abnormality may be labeled with text.

At optional decision 320, computer-executable instructions stored on a memory of a device, such as a server and/or computer of an ultrasound system, may be executed to determine whether additional views of the abnormality are required. For example, when an abnormality is determined to be present, it may be desirable to generate additional imaging to further analyze the abnormality. Conversely, when it is determined that an abnormality is absent, it may be desirable to generate additional images to further confirm that the abnormality is absent. Whether or not additional views are required may be dependent on the type of abnormality detected and may be predetermined (e.g., if a certain abnormality is detected then the system may automatically request certain additional views). If additional views are not required at decision 320, then block 302 and/or 304 may be reinitiated. Alternatively, if additional views of the abnormality are required, then at optional block 322 computer-executable instructions stored on a memory of a device, such as a server and/or computer of an ultrasound system, may be executed to present a request for additional views of the abnormality and block 304 may be reinitiated. Where the image data analyzed at block 312 is the entire video clip, decision 320 and block 322 may be skipped after block 318.

While various illustrative embodiments of the invention are described above, it will be apparent to one skilled in the art that various changes and modifications may be made therein without departing from the invention. The appended claims are intended to cover all such changes and modifications that fall within the true scope of the invention.

What is claimed is:

1. A system for analysis of fetal ultrasound images, the system comprising:
   memory configured to store computer-executable instructions; and
   at least one computer processor configured to access memory and execute the computer-executable instructions to:
      receive image data corresponding to data generated by an ultrasound system, the image data comprising a plurality of frames forming one or more video clip and showing a portion of fetal anatomy;
      determine a machine learning model comprising one or more neural networks trained to analyze the one or more video clip and generate outputs indicative of one or more of contours or coordinates corresponding to anatomy;
      analyze the image data using the machine learning model to generate at least one output, the at least one output indicative of at least one of first contours or first coordinates corresponding to the portion of fetal anatomy;
      determine a first value corresponding to the fetal anatomy and based on the at least one output;
      determine, based on the first value, an increased likelihood of a presence of a morphological abnormality in the fetal anatomy as compared to a default likelihood corresponding to the morphological abnormality, the morphological abnormality associated with a threshold value;
      generate an adjusted threshold value for the morphological abnormality based on the first value corresponding to the increased likelihood of the presence of a morphological abnormality; and
      replace a default threshold value associated with the morphological abnormality with the adjusted threshold value.

2. The system of claim 1, wherein the at least one computer processor is further configured to access memory and execute the computer-executable instructions to:
   compare the first value to a first threshold value; and
   determine the first value does not satisfy a first threshold value.

3. The system of claim 2, wherein the at least one computer processor is further configured to access memory and execute the computer-executable instructions to determine an increased likelihood of the presence of the morphological abnormality is based on the first value not satisfying the first threshold value.

4. The system of claim 1, wherein the at least one computer processor is further configured to access memory and execute the computer-executable instructions to:
   determine a score indicative of a difference between the first value and a default value corresponding to one or more patients different than the patient;
   compare the score to a first threshold value; and
   determine the score does not satisfy a first threshold value.

5. The system of claim 4, wherein determining the increased likelihood of the presence of the morphological abnormality is based on the score not satisfying the first threshold value.

6. The system of claim 1, wherein the first value corresponds to a length, volume, or area of a feature of the fetal anatomy.

7. The system of claim 1, wherein the portion of anatomy is a portion of cardiovascular anatomy.

8. The system of claim 1, wherein the at least one output is indicative of a second value different than a first value, the second value corresponding to a second length, volume or area of a feature of the fetal anatomy.

9. The system of claim 8, wherein the at least one computer processor is further configured to access memory and execute the computer-executable instructions to:
   determine that the second value does not satisfy the adjusted threshold value; and
   determine that the morphological abnormality corresponding to the adjusted threshold value is present based on the second value not satisfying the adjusted threshold value.

10. The system of claim 1, wherein the morphological abnormality is one of enlarged cardiothoracic ratio, right ventricular to left ventricular size discrepancy, tricuspid valve to mitral valve annular size discrepancy, cardiac axis deviation, pulmonary valve to aortic valve annular size discrepancy, overriding artery, septal defect at a cardiac crux, or abnormal relationship of outflow tracts.

11. A computer implemented method for analysis of fetal ultrasound images corresponding to a patient, the computer implemented method comprising:
   receiving image data corresponding to data generated by an ultrasound system, the image data comprising a plurality of frames forming one or more video clip and showing a portion of fetal anatomy;

determining a machine learning model comprising one or more neural networks trained to analyze the one or more video clip and generate outputs indicative one or more of contours or coordinates corresponding to anatomy;

analyzing the image data using the machine learning model to generate at least one output, the at least one output indicative of one or more of first contours or first coordinates corresponding to the portion of fetal anatomy;

determining a first value of the fetal anatomy based on the at least one output;

determining, based on the first value, an increased likelihood of a presence of a morphological abnormality in the fetal anatomy as compared to a default likelihood corresponding to the morphological abnormality, the morphological abnormality associated with a threshold value;

generating an adjusted threshold value for the morphological abnormality based on the first value corresponding to the increased likelihood of the presence of a morphological abnormality; and replacing a default threshold value associated with the morphological abnormality with the adjusted threshold value.

12. The computer implemented method of claim 11, further comprising
comparing the first value to a first threshold value; and
determining the first value does not satisfy a first threshold value.

13. The computer implemented method of claim 12, wherein determining an increased likelihood of the presence of the morphological abnormality is based on the first value not satisfying the first threshold value.

14. The computer implemented method of claim 11, further comprising:

determining a score indicative of a difference between the first value and a default value corresponding to one or more patients different than the patient;
comparing the score to a first threshold value; and
determining the score does not satisfy a first threshold value.

15. The computer implemented method of claim 14, wherein determining the increased likelihood of the presence of the morphological abnormality is based on the score not satisfying the first threshold value.

16. The computer implemented method of claim 11, wherein the first value corresponds to a length, volume, or area of a feature of the fetal anatomy.

17. The computer implemented method of claim 11, wherein the portion of anatomy is a portion of cardiovascular anatomy.

18. The computer implemented method of claim 11, wherein the at least one output is indicative of a second value different than a first value, the second value corresponding to a second length, volume or area of a feature of the fetal anatomy.

19. The computer implemented method of claim 18, further comprising:
determining that the second value does not satisfy the adjusted threshold value; and
determining that the morphological abnormality corresponding to the adjusted threshold value is present based on the second value not satisfying the adjusted threshold value.

20. The computer implemented method of claim 11, wherein the morphological abnormality is one of enlarged cardiothoracic ratio, right ventricular to left ventricular size discrepancy, tricuspid valve to mitral valve annular size discrepancy, cardiac axis deviation, and pulmonary valve to aortic valve annular size discrepancy, overriding artery, septal defect at a cardiac crux, or abnormal relationship of outflow tracts.

* * * * *